United States Patent
Black et al.

[11] Patent Number: 5,925,631
[45] Date of Patent: Jul. 20, 1999

[54] ALKYLATED STYRENES AS PRODRUGS TO COX-2 INHIBITORS

[75] Inventors: Cameron Black, Pointe Claire; Greg Hughes, Bridgewater; Erich Grimm, Baie d'Urfe; Serge Leger, Dollard des Ormeaux; Petpiboon Prasit, Kirkland; Zhaoyin Wang, Pierrefonds, all of Canada

[73] Assignee: Merck & Co., Inc., Rahway, N.J.

[21] Appl. No.: 09/128,140

[22] Filed: Aug. 3, 1998

Related U.S. Application Data

[62] Division of application No. 08/786,517, Jan. 21, 1997., Pat. No. 5,789,413

[60] Provisional application No. 60/010,432, Feb. 1, 1996.

[51] Int. Cl.⁶ .............. C07D 209/44; C07D 213/30; C07D 217/16; C07D 211/22; C07D 307/32; A61K 31/44; A61K 31/445; A61K 31/47

[52] U.S. Cl. ............. 514/183; 514/255; 514/256; 514/307; 514/317; 514/357; 514/365; 514/374; 514/406; 514/427; 514/438; 514/461; 544/179; 544/224; 544/242; 544/336; 546/141; 546/236; 546/237; 546/238; 546/300; 546/301; 548/204; 548/236; 548/253; 548/373.1; 548/375.1; 548/482; 548/560; 548/561; 549/77; 549/79; 549/80; 549/496

[58] Field of Search .................... 514/183, 255, 514/256, 307, 317, 357, 365, 374, 406, 427, 438, 461; 544/179, 224, 242, 336; 546/141, 236, 237, 238, 300, 301; 548/204, 253, 236, 373.1, 375.1, 482, 560, 561; 549/77, 79, 80, 496

[56] References Cited

U.S. PATENT DOCUMENTS 5,393,790  2/1995  Reitz et al. ............... 514/709

FOREIGN PATENT DOCUMENTS 424541    5/1991  European Pat. Off. .
WO 95/00501  1/1995  WIPO .

*Primary Examiner*—Mukund J. Shah
*Assistant Examiner*—Deepak R. Rao
*Attorney, Agent, or Firm*—Richard C. Billups; Curtis C. Panzer; David L. Rose

[57] ABSTRACT

The invention encompasses the novel compound of Formula I useful in the treatment of cyclooxygenase-2 mediated diseases.

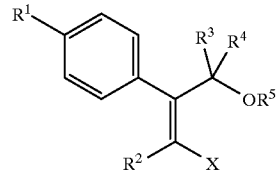

The invention also encompasses certain pharmaceutical compositions for treatment of cyclooxygenase-2 mediated diseases comprising compounds of Formula I.

12 Claims, No Drawings

ALKYLATED STYRENES AS PRODRUGS TO COX-2 INHIBITORS

CROSS REFERENCE TO RELATED APPLICATIONS

This application is a division of U.S. application Ser. No. 08/786,517 filed on Jan. 21, 1997, now U.S. Pat. No. 5,789,413, which was based upon Provisional application No. 60/010,432 filed on Feb. 1, 1996, priority of which is claimed hereunder.

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

A brief description of the potential utility of cyclooxygenase-2 inhibitors is given in an article by John Vane, *Nature*, Vol. 367, pp. 215–216, 1994, and in an article in *Drug News and Perspectives*, Vol. 7, pp. 501–512, 1994.

A number of stilbene derivatives are known in the chemical literature. Toda et al., in *Chem. Commun.* 1234–5 (1984) describe the dialdehydes A and the diol B is described by Tsuji et al., *J. Am. Chem. Soc.* 88, 1289–92 (1966), and diol C was prepared by Dhawau et al., *J. Org. Chem.*, 45, 922–4 (1980). No utility is disclosed for these compounds, nor do they carry the $R^1$ substituent of the present invention.

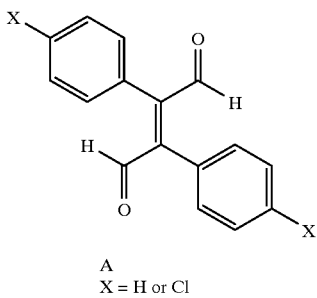

A
X = H or Cl

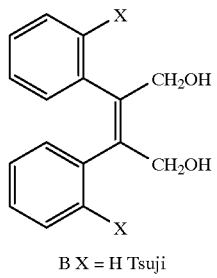

B X = H Tsuji
C X = Cl Dhawan

Structure D is disclosed as having usefulness for treating hyperlipidemia by Hashimoto et al., European Patent Application 424,541 (May 2, 1991).

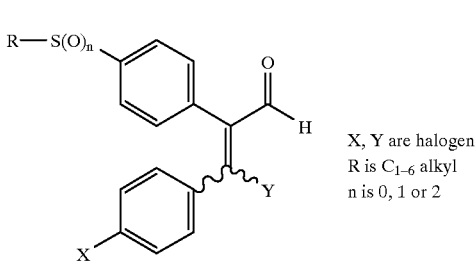

D

X, Y are halogen
R is $C_{1-6}$ alkyl
n is 0, 1 or 2

These compounds (D) lack the second carbon substituent X of the present invention and have an unrelated utility.

SUMMARY OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I. These compounds are prodrugs of compounds which inhibit COX-2 selectively over COX-1. The prodrugs are converted in vivo to the selective inhibitors.

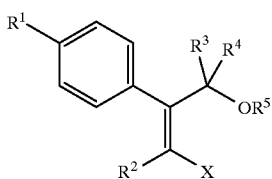

The invention also encompasses certain pharmaceutical compositions for treatment of COX-2 mediated diseases comprising compounds of Formula I.

DETAILED DESCRIPTION OF THE INVENTION

The invention encompasses the novel compound of Formula I as well as a method of treating COX-2 mediated diseases comprising administration to a patient in need of such treatment of a non-toxic therapeutically effective amount of a compound of Formula I

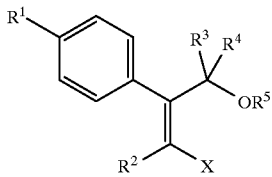

or pharmaceutically acceptable salts thereof wherein
X is
  (a) $CH_2OR^6$,
  (b) $C(O)R^7$,
  (c) $CH_2C(O)CH_3$, or
  (d) $CH_2CH_2COR^7$;
$R^1$ is selected from the group consisting of
  (a) $S(O)_2CH_3$,
  (b) $S(O)_2NH_2$,
  (c) $S(O)_2NHC(O)CF_3$,
  (d) $S(O)(NH)CH_3$,
  (e) $S(O)(NH)NH_2$, and
  (f) $S(O)(NH)NHC(O)CF_3$;
$R^2$ is selected from the group consisting of
  (a) $NR^8R^9$,
  (b) $SR^9$,
  (c) $OR^9$,
  (d) $R^9$,
  (e) $C_{2-10}$alkenyl,
  (f) $C_{2-10}$alkynyl,
  (g) a mono-, di-, tri- or tetra-substituted heterocycloalkyl group of 5, 6 or 7 members which contains 1 or 2 heteroatoms chosen from O, S, or N and optionally contains a carbonyl group or a sulfonyl group the said substituents are selected from the group consisting of
    (1) halo,
    (2) $C_{1-10}$alkyl,
    (3) $C_{1-10}$alkoxy,
    (4) $C_{1-10}$alkylthio,
    (5) CN,
    (6) $CF_3$, and
    (7) $C(CH_3)_2OH$,
  (h) styryl or substituted styryl wherein the substituent is selected from the group consisting of
    (1) halo,
    (2) $C_{1-6}$alkoxy,
    (3) $C_{1-6}$alkylthio,
    (4) CN,
    (5) $CF_3$,
    (6) $C_{1-10}$alkyl,
    (7) —$CO_2H$,
    (8) —$C(CH_3)_2OH$, and
    (9) benzyloxy,
  (i) phenylacetylene or substituted phenylacetylene wherein the substituent is selected from the group consisting of
    (1) halo,
    (2) $C_{1-6}$alkoxy,
    (3) $C_{1-6}$alkylthio,
    (4) CN,
    (5) $CF_3$,
    (6) $C_{1-10}$alkyl,
    (7) —$CO_2H$,
    (8) —$C(CH_3)_2OH$,
    (9) benzyloxy, and
  (j) $C_{1-10}$ fluoroalkenyl;
$R^3$ and $R^4$ are each independently $C_{1-10}$alkyl, $CH_2OR^8$, CN, or $C_{1-6}$fluoroalkyl, unsubstituted or mono- or di-substituted phenyl, unsubstituted or mono- or di-substituted benzyl, unsubstituted or mono- or di-substituted heteroaryl, unsubstituted or mono or di-substituted heteroarylmethyl, wherein the substituents are selected from the group consisting of
  (1) halo,
  (2) $C_{1-10}$alkyl,
  (3) $C_{1-10}$alkoxy,
  (4) $C_{1-10}$alkylthio,
  (5) CN, and
  (6) $CF_3$,
or $R^3$ and $R^4$ together with the carbon to which they are attached may form a saturated monocyclic ring of 3, 4, 5, 6, or 7 members which may optionally contain one or two heteroatoms chosen from O, S or N;
$R^5$ is selected from the group consisting of
  (a) hydrogen,
  (b) $C_{1-6}$alkyl, and
  (c) $C(O)R^{10}$;
$R^6$ is selected from the group consisting of
  (a) hydrogen,
  (b) $C_{1-6}$alkyl, and
  (c) $C(O)R^{10}$;
$R^7$ is selected from the group consisting of
  (a) hydrogen,
  (b) OH,
  (c) $NH_2$,
  (d) $OR^{10}$,
  (e) $NHR^{10}$,
  (f) $NR^{10}R^{11}$,
$R^8$ is independently selected from the group consisting of
  (a) hydrogen and
  (b) $R^9$;
$R^9$ is selected from the group consisting of
  (a) $C_{1-10}$alkyl,
  (b) unsubstituted or mono-, di- or tri-substituted phenyl or naphthyl wherein the substituent is selected from the group consisting of (1) halo,
(2) $C_{1-10}$alkoxy,
(3) $C_{1-10}$alkylthio,
(4) CN,
(5) $CF_3$,
(6) $C_{1-10}$alkyl,
(7) —$CO_2H$,
(8) benzyloxy,
(c) unsubstituted or mono-, di- or tri-substituted heteroaryl 1 5 wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2, 3, or 4 additional N atoms, said substituents are selected from the group consisting of
(1) halo,
(2) $C_{1-10}$alkyl,
(3) $C_{1-10}$alkoxy,
(4) $C_{1-10}$alkylthio,
(5) CN,
(6) $CF_3$,
(d) an unsubstituted or a mono- or di- substituted benzoheterocycle in which the heterocycle is a 5, 6, or 7-membered ring which may contain 1 or 2 heteroatoms chosen independently from O, S, or N and which may contain a carbonyl group or a sulfonyl group; the said substituents are selected from the group consisting of
(1) halo,
(2) $C_{1-10}$alkyl,
(3) $C_{1-10}$alkoxy,
(4) $C_{1-10}$alkylthio,
(5) CN, and
(6) $CF_3$,
(e) an unsubstituted or a mono- or di- substituted benzocarbocycle in which the carbocycle is a 5, 6, or 7-membered ring which optionally contains a carbonyl group, the said substituents are selected from the group consisting of
(1) halo,
(2) $C_{1-10}$alkyl,
(3) $C_{1-10}$alkoxy,
(4) $C_{1-10}$alkylthio,
(5) CN, and
(6) $CF_3$,
(f) a mono- or di-substituted bicyclic heteroaryl or 8, 9, or 10 members, containing 2 to 5 heteroatoms chosen independently from O, S or N, and in which each ring contains at least one heteroatom, wherein the substituents are selected from the group consisting of
(1) hydrogen,
(2) halo,
(3) $C_{1-10}$alkyl,
(4) $C_{1-10}$alkoxy,
(5) $C_{1-10}$alkylthio,
(6) CN, and
(7) $CF_3$,
$R^{10}$ and $R^{11}$ are independently chosen from the group consisting of
(a) $C_{1-10}$alkyl
(b) $C_{1-10}$alkyl-$CO_2R^{12}$
(c) $C_{1-10}$alkyl-$NR^{12}R^{13}$
(d) $(CH_2CH_2O)_nR^{12}$, where n=1 to 200
(e) $(CH_2CH_2O)_nCH_2CH_2NR^{12}R^{13}$, where n=1 to 200
or $R^{10}$ and $R^{11}$ together with the nitrogen to which they are attached may form a monocyclic ring of 3, 4, 5, 6, or 7 members which may optionally contain an additional one or two heteroatoms chosen from O, S or N—$R_{12}$;
$R^{12}$ and $R^{13}$ are independently chosen from the group consisting of
(a) hydrogen, and
(b) $C_{1-10}$alkyl.
A preferred genus of compounds within this embodiment is that wherein
X is
(a) $CH_2OR^6$,
(b) $C(O)R^7$,
$R^1$ is selected from the group consisting of
(a) $S(O)_2CH_3$,
(b) $S(O)_2NH_2$,
(c) $S(O)_2NHC(O)CF_3$,
$R^2$ is an unsubstituted or mono-, di- or tri-substituted phenyl or naphthyl wherein the substituent is selected from the group consisting of
(1) halo,
(2) $C_{1-3}$alkoxy,
(3) $CF_3$, and
(4) $C_{1-3}$alkyl;
$R^3$ and $R^4$ are independently $C_{1-3}$ alkyl or $C_{1-3}$ fluoroalkyl, or $R^3$ and $R^4$ together with the carbon to which they are attached may form a monocyclic ring of 3, 4, 5, or 6 members which may optionally contain a heteroatom chosen from O, or S;
$R^5$ is selected from the group consisting of
(a) hydrogen,
(b) $C_{1-3}$alkyl,
(c) $C(O)R^{10}$;
$R^6$ is selected from the group consisting of
(a) hydrogen,
(b) $C_{1-3}$alkyl,
(c) $C(O)R^{10}$;
$R^7$ is selected from the group consisting of
(b) OH,
(c) $NH_2$,
(d) $OR^{10}$,
(e) $NHR^{10}$,
(f) $NR^{10}R^{11}$;
$R^{10}$ and $R^{11}$ are independently chosen from the group consisting of
(a) $C_{1-3}$alkyl,
(b) $C_{1-6}$alkyl-$CO_2R^{12}$,
(c) $C_{1-6}$alkyl-$NR^{12}R^{13}$,
(d) $(CH_2CH_2O)_nR^{12}$, where n=1 to 200
(e) $(CH_2CH_2O)_nCH_2CH_2NR^{12}R^{13}$, where n=1 to 200
or $R^{10}$ and $R^{11}$ together with the nitrogen to which they are attached may form a monocyclic ring of 3, 4, 5, 6, or 7 members which may optionally contain an additional heteroatom chosen from O, S or N-$R^{12}$;
$R^{12}$ and $R^{13}$ are independently chosen from the group consisting of
(a) hydrogen, and
(b) $C_{1-10}$alkyl.
Another preferred genus within this embodiment is that wherein $R^2$ is $R^9$. Within this genus is a preferred sub-genus wherein $R^9$ is an unsubstituted or mono-, di-, or tri-substituted phenyl wherein the substituent is selected from the group consisting of (1) halo,
(2) $C_{1-10}$alkyl,
(3) $C_{1-10}$alkoxy,
(4) $C_{1-10}$alkylthio,
(5) CN
(6) $CF_3$
(7) —COOH, and
(8) benzyloxy.

Another preferred genus within this embodiment is that wherein
$R^1$ is selected from the group consisting of
(a) $S(O)_2CH_3$, and
(b) $S(O)_2NH_2$.

Within this genus there is a sub-genus wherein $R^1$ is $S(O)_2CH_3$.

Another preferred genus within this embodiment is that wherein
$R^3$ and $R^4$ are each independently $C_{1-3}$alkyl. A sub-genus within this group is that wherein each of $R^3$ and $R^4$ is independently chosen from the group consisting of
(a) methyl
(b) ethyl.

For purposes of this specification alkyl, alkenyl and alkynyl mean linear branched and cyclic structures, and combinations thereof, containing the indicated number of carbon atoms.

Examples of alkyl groups are methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl- 4-propylnonyl, cyclopropyl, cyclopentyl, cycloheptyl, adamantyl, cyclododecylmethyl, 2-ethyl-1-bicyclo[4.4.0]decyl and the like.

Examples of alkenyl groups are vinyl, allyl, isopropenyl, pentenyl, hexenyl, heptenyl, 1-propenyl, 2-butenyl, 2-methyl-2-butenyl, 5-decen-1-yl, 2-dodecen-1-yl, 4-cyclopentenylmethyl, 1-cyclohexenyl, and the like.

Examples of alkynyl groups are ethynyl, propargyl, 3-methyl-1-pentyn-1-yl, 2-heptyn-1-yl, 2-pentadecyn-1-yl, 2-(cyclopropyl)acetylen-1-yl, cyclodecyn-3-yl, and the like. The alkynyl triple bond may be located anywhere in the group, with the proviso that if it is within a ring, such a ring must be 10 members or greater.

For purposes of this specification fluoro alkyl means alkyl groups of the indicated number of carbon atoms in which one hydrogen or more is replaced by fluorine. Examples are —$CF_3$, —$CH_2CH_2F$, —$CH_2CF_3$, c-Pr-$F_5$, c-Hex-$F_{11}$ and the like.

Fluoroalkenyl means alkenyl groups in which one hydrogen or more is replaced by fluorine. Examples are —CH=$CF_2$, —CH=CH$CF_3$, —C($CF_3$)=$CMe_2$, —CH=C($CH_3$)$CH_2CF_3$, —CH=CH($CH_2F$) and the like.

For purposes of this specification alkoxy means alkoxy groups of the indicated number of carbon atoms of a straight, branched, or cyclic configuration. Examples of alkoxy groups are methoxy, ethoxy, propoxy, isopropoxy, cyclopropyloxy, cyclopentylmethoxy, cyclohexyloxy, and the like.

For purposes of this specification alkylthio means alkylthio groups of the indicated number of carbon atoms of a straight, branched or cyclic configuration. Examples of alkylthio groups are methylthio, propylthio, isopropylthio, cyclopropylmethylthio, cycloheptylthio, etc. By way of illustration, the propylthio group signifies —$SCH_2CH_2CH_3$.

For purposes of this specification, in situations in which a term occurs two or more times, the definition of the term in each occurrence is independent of the definition in each additional occurrence. For purposes of this specification Halo means F, Cl, Br, or I.

For purposes of this specification heteroaryl as in $R^3$ and $R^9$ is intended to include, but is not limited to
(1) furanyl,
(2) diazinyl,
(3) imidazolyl,
(4) isooxazolyl,
(5) isothiazolyl,
(6) oxadiazolyl,
(7) oxazolyl,
(8) pyrazolyl,
(9) pyridyl,
(10) pyrrolyl,
(11) tetrazinyl
(12) tetrazolyl,
(13) thiadiazolyl,
(14) thiazolyl,
(15) thienyl,
(16) triazinyl, and
(17) triazolyl.

Similarly, for purposes of this specification cyclic groups such as a heterocycloalkyl or benzocarbocycle or benzoheterocycle such as in $R^2$ and $R^9$ is intended to include, but is not limited to:
(1) tetrahydrothiopyranyl,
(2) thiomorpholinyl,
(3) pyrrolidinyl,
(4) hexahydroazepinyl,
(5) indanyl,
(6) tetralinyl,
(7) indolyl,
(8) benzofuranyl,
(9) benzothienyl,
(10) benzimidazolyl,
(11) benzothiazolyl,

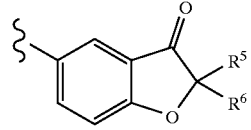

(12)

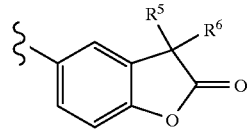

(13)

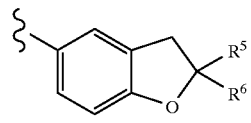

(14)

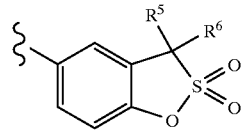

(15)

(16) 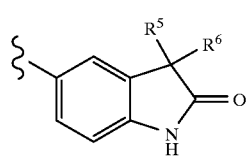
(17) 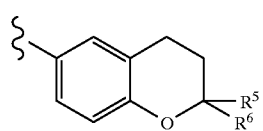
(18) 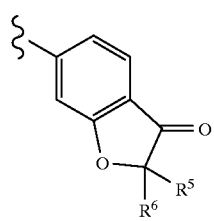
(19) 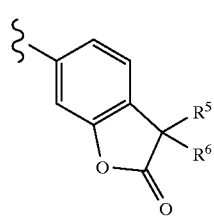
(20) 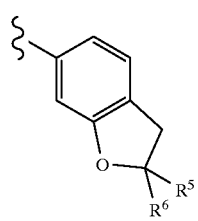
(21) 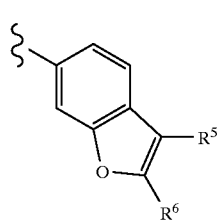
(22) 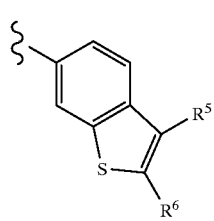
(23) 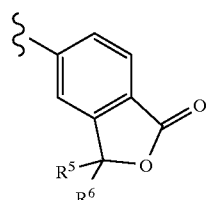
(24) 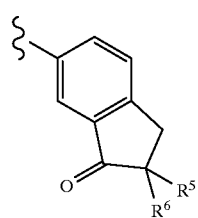
(25) 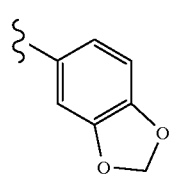
(26) 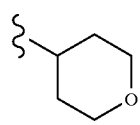
(27) 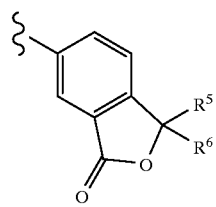
(28) 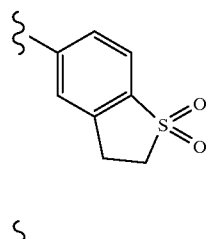
(29) 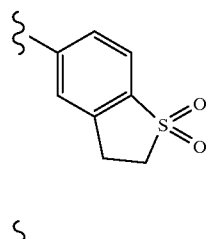

(30) 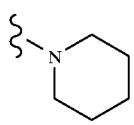
(31) 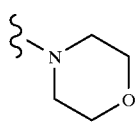
(32) 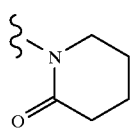
(33) 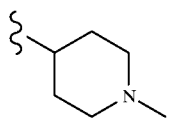
Similarly, for purposes of this specification bicyclic heteroaryl as in R² is intended to include, but is not limited to optionally mono- or di-substituted
(1) 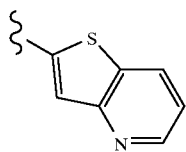
(2) 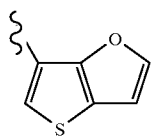
(3) 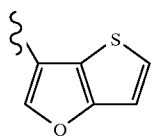
(4) 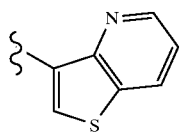
(5) 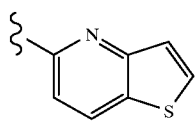
(6) 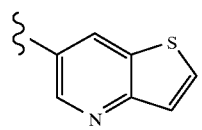
(7) 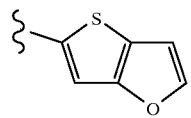
(8) 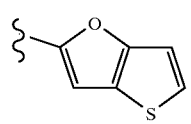
(9) 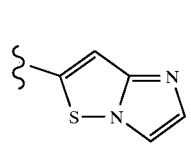
(10) 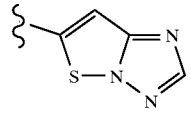
(11) 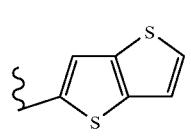
(12) 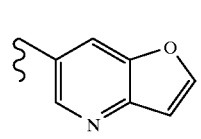
(13) 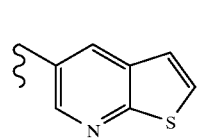
(14) 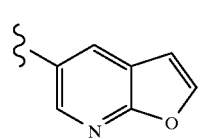
(15) 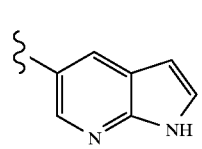

(16) 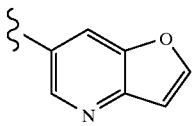

(17) 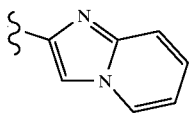

(18) 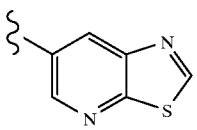

(19) 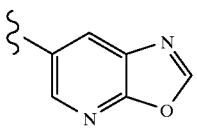

(20) 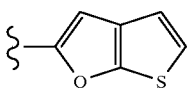

(21) 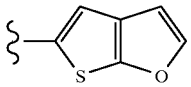

The following abbreviations have the indicated meanings:
AA=arachidonic acid
Ac=acetyl
AIBN=2.2'-azobisisobutyronitrile
BOP=Benzotriazol-1-yloxy-tris(dimethylamino)-phosphonium hexafluorophosphate
Bn=benzyl
CHO=chinese hamster ovary
CMC=1-cyclohexyl-3-(2-morpholinoethyl) carbodiimidemetho-p-toluenesulfonate
COX=cyclooxygenase
DBU=diazabicyclo[5.4.0]undec-7-ene
DMAP=4-(dimethylamino)pyridine
DMF=N,N-dimethylformamide
DMSO=dimethyl sulfoxide
$Et_3N$=triethylamine
HATU=O-(7-azabenzotriazol-1-yl)-1,1,3,3-tetramethyluronium hexfluorophosphate
HBSS=Hanks balanced salt solution
HEPES=N-[2-Hydroxyethyl]piperazine-$N^1$-[2-ethanesulfonic acid]
HWB=human whole blood
KHMDS=potassium hexamethyldisilazane
LDA=lithium diisopropylamide
LPS=lipopolysaccharide
mCPBA=metachloro perbenzoic acid
MMPP=magnesium monoperoxyphthalate
Ms=methanesulfonyl=mesyl
MsO=methanesulfonate=mesylate
NBS=N-bromosuccinimide
NCS=N-chlorosuccinimide
NIS=N-iodosuccinimide
NSAID=non-steroidal anti-inflammatory drug
Oxone®=potassium peroxymonosulfate
PCC=pyridinium chlorochromate
PDC=pyridinium dichromate
r.t.=room temperature
rac.=racemic
Tf=trifluoromethanesulfonyl=triflyl
TFAA=trifluoroacetic anhydride
TfO=trifluoromethanesulfonate=triflate
THF=tetrahydrofuran
TLC=thin layer chromatography
TMPD=N,N,N',N'-tetramethyl-p-phenylenediamine
Ts=p-toluenesulfonyl=tosyl
TsO=p-toluenesulfonate=tosylate
Tz=1H (or 2H)-tetrazol-5-yl
$SO_2Me$=methyl sulfone (also $SO_2CH_3$)
$SO_2NH_2$=sulfonamide

| Alkyl group abbreviations | | Dose Abbreviations |
|---|---|---|
| Me = | methyl | bid = bis in die = twice daily |
| Et = | ethyl | qid = quater in die = four times a day |
| n-Pr = | normal propyl | |
| i-Pr = | isopropyl | tid = ter in die = three times a day |
| n-Bu = | normal butyl | |
| i-Bu = | isobutyl | |
| s-Bu = | secondary butyl | |
| t-Bu = | tertiary butyl | |
| c-Pr = | cyclopropyl | |
| c-Bu = | cyclobutyl | |
| c-Pen = | cyclopentyl | |
| c-Hex = | cyclohexyl | |

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumour growth and hence can be used in the treatment of cancer. Compound 1 may also be of use in the treatment and/or prevention of cyclooxygenase-mediated proliferative disorders such as may occur in diabetic retinopathy and tumour angiogenesis.

Compound I, by virtue of its in vivo conversion to a COX-2 inhibitor, will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis), and for treatment of glaucoma.

The compounds of Formula I are prodrugs of selective COX-2 inhibitors, and exert their action by conversion in vivo to these active and selective COX-2 inhibitors. The active compounds formed from the compounds of the present invention are described in the following documents which are hereby encorporated by reference:

WO 95/00501, published Jan. 5, 1995, WO 95/18799, published Jul. 13, 1995 and U.S. Pat. No. 5,474,995, published Dec. 12, 1995.

In certain respects, compounds of the present invention have advantages over the compounds described in these documents by virtue of improved pharmacokinetic and/or safety profiles. A general description of the advantages and uses of prodrugs as pharmaceutically useful compounds is given in an article by Waller and George in *Br. J. Clin. Pharmac.* Vol. 28, pp. 497–507, 1989.

By way of illustration, the following compounds of the present invention are converted to the indicated COX-2 selective inhibitors.

regional enteritis, ulcerative colitis, diverticulitis or with a recurrent history of gastrointestinal lesions; GI bleeding, coagulation disorders including anaemia such as hypoprothrombinemia, haemophilia or other bleeding problems; kidney disease; those prior to surgery or taking anticoagulants.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred

| Example | Prodrug | Active Drug | Reference |
|---|---|---|---|
| 1 | [structure with HO, HO, SO₂Me, F substituents] | [furanone structure with SO₂Me, F] | WO 95/18799 |
| 3 | [structure with MeO, NaO, SO₂Me, F] | [furanone structure with SO₂Me, F] | WO 95/18799 |
| 4 | [structure with MeO, Me₂N, SO₂Me, F] | [furanone structure with SO₂Me, F] | WO 95/18799 |
| 6 | [structure with MeO, MeO, SO₂Me, F] | [furanone structure with SO₂Me, F] | WO 95/18799 |

By virtue of its in vivo conversion to a compound with high inhibitory activity against COX-2 and/or a specificity for COX-2 over COX-1, compound I will prove useful as an alternative to conventional NSAID'S, particularly where such non-steroidal antiinflammatory drugs may be contraindicated such as in patients with peptic ulcers, gastritis, are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N- dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like, and basic ion exchange resins.

It will be understood that in the discussion of methods of treatment which follows, references to the compounds of Formula I are meant to also include the pharmaceutically acceptable salts.

The compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease, and for the prevention of bone loss (treatment of osteoporosis) and for the treatment of glaucoma.

By virtue of the high COX-2 activity and/or specificity for COX-2 of the inhibitor derived from I over COX-1, Compound I will prove useful as an alternative to conventional NSAID's, particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Compound I, will be useful as a partial or complete substitute for conventional NSAID'S in preparations wherein they are presently co-administered with other agents or ingredients. Thus in further aspects, the invention encompasses pharmaceutical compositions for treating COX-2 mediated diseases as defined above comprising a non-toxic therapeutically effective amount of the compound of Formula I as defined above and one or more ingredients such as another pain reliever including acetominophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a prostaglandin including misoprostol, enprostil, rioprostil, ornoprostol or rosaprostol; a diuretic; a sedating or non sedating antihistamine. In addition the invention encompasses a method of treating cyclooxygenase mediated diseases comprising: administration to a patient in need of such treatment a non-toxic therapeutically effective amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating COX-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents,. for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed (for purposes of this application, topical application shall include mouth washes and gargles). Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods Method A:

An aryl lactone II is reduced to the diol III by a suitable reducing agent such as diisobutyl aluminum hydride followed by lithium aluminum hydride in an appropriate solvent such as toluene, hexane, tetrahydrofuran or ether. This material may be treated with an oxidizing agent such as MMPP or mCPBA to produce the sulfone Ia, which is an example of the present invention. Alternatively, III is selectively silylated with a silyl chloride or triflate in the presence of a base such as imidazole or di-t-butylpyridine to give IV. The remaining tertiary alcohol can be alkylated to give V using an alkylating agent $R^5X$ such as an alkyl halide or tosylate in the presence of a base such as sodium hydride. Alternatively, $R^5X$ may be an acylating reagent such as an acid anhydride or acid chloride which can be used with an appropriate base to obtain the acyl derivative V. The silyl group can then be removed using a fluoride source such as TBAF or HF to give VI. At this point, the methylthio ether can be oxidized to the methyl sulfone Ib using an oxidant such as MMPP or mCPBA. The primary alcohol is then converted to the corresponding acid Ic under appropriate oxidizing conditions such as oxalyl chloride/DMSO/$Et_3N$ followed by sodium chlorite. This acid is an example of the present invention and may be esterified to give Id by treatment with an alcohol and an appropriate coupling agent such as HATU. The methyl ester is conveniently prepared on small scale by the reaction of Ic with diazomethane in ether. Alternatively, the amide Ie may be formed from acid Ic by treatment with ammonia, or a primary or secondary amine in the presence of a coupling reagent such as HATU.

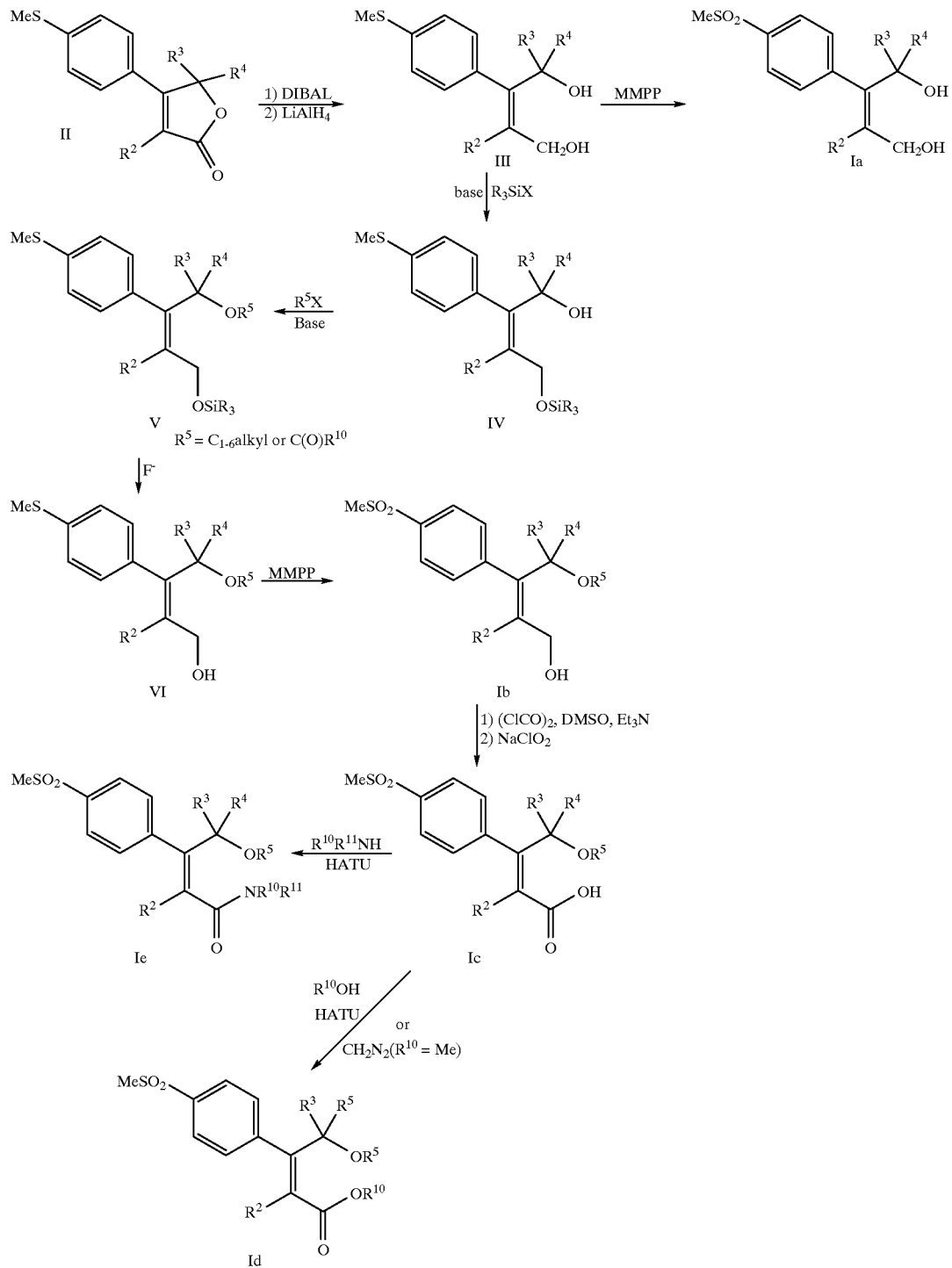
Method B
Ia may be acylated using an appropriate anhydride or acid chloride in the presence of a base such as triethylamine or pyridine/DMAP to give the bis-acyl derivative If.

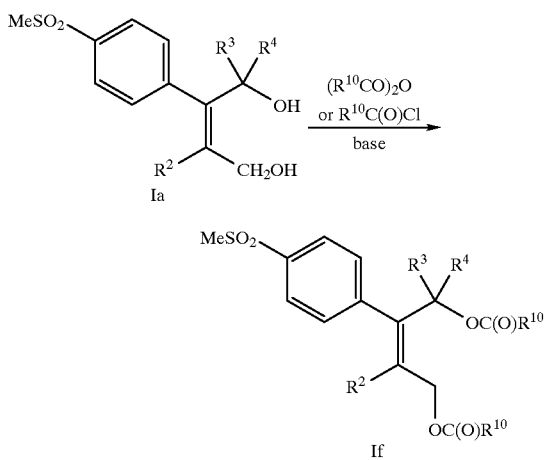
REPRESENTATIVE COMPOUNDS
In Table I are shown some lactones from which the compounds of the present invention can be prepared according to Method A.
In Table II are shown compounds representative of the present invention (structures Ia–f).
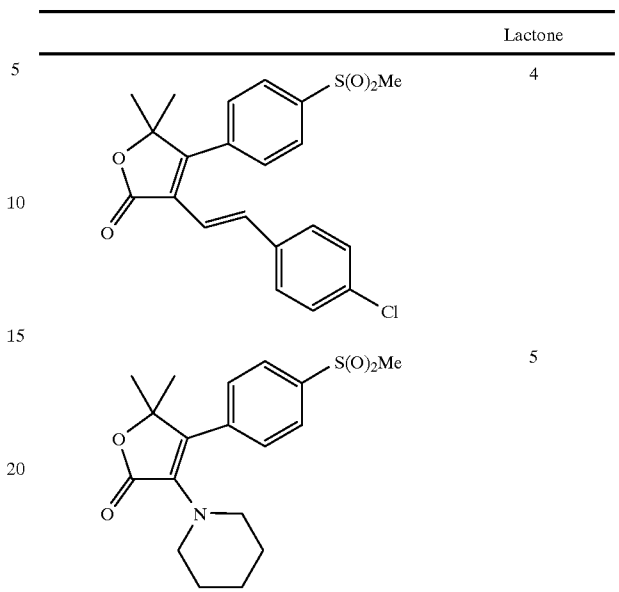

TABLE I-continued
| | Lactone |
|---|---|
| 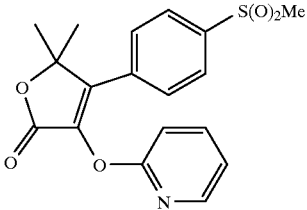 | 10 |
| 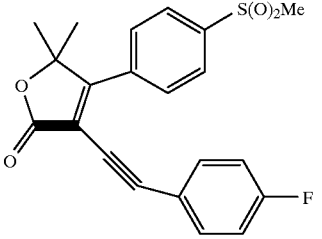 | 11 |
TABLE I-continued
| | Lactone |
|---|---|
| 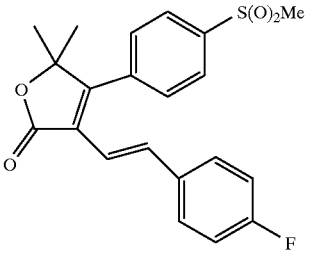 | 12 |
TABLE II
| | EXAMPLE |
|---|---|
| 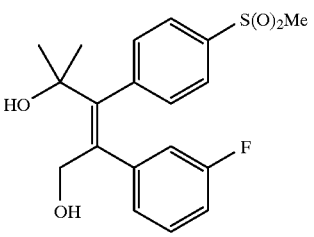 | 1 |
| 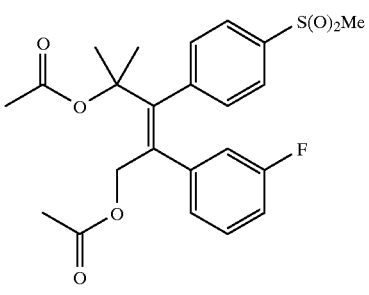 | 2 |
| 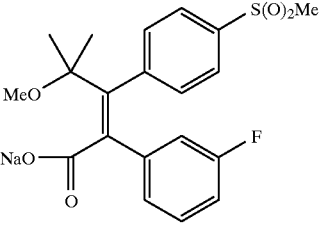 | 3 |

TABLE II-continued

| | EXAMPLE |
|---|---|
| (structure) | 4 |
| (structure) | 5 |
| (structure) | 6 |
| (structure) | 7 |
| (structure) | 8 |
| (structure) | 9 |

TABLE II-continued

| | EXAMPLE |
|---|---|
| (structure) | 10 |
| (structure) | 11 |
| (structure) | 12 |
| (structure) | 13 |
| (structure) | 14 |
| (structure) | 15 |

TABLE II-continued

EXAMPLE

[Structure: (E)-2-(3-fluorophenyl)-3-(4-(methylsulfonyl)phenyl)-4,4-dimethylpent-2-enoic acid type structure with HO₂C, tert-butyl-like group, S(O)₂Me on para phenyl and F on meta phenyl]

[Structure: similar alkene with HO-C(Me)₂- group, CH₂CH₂CO₂H chain, S(O)₂Me-phenyl and F-phenyl substituents]

[Structure: similar alkene with HO-C(Me)₂- group, CH₂C(=O)CH₃ ketone chain, S(O)₂Me-phenyl and F-phenyl substituents]

Assays for determining Biological Activity

The compound of Formula I can be tested using the following assays to determine their cyclooxygenase-2 inhibiting activity.

INHIBITION OF CYCLOOXYGENASE ACTIVITY

Compounds are tested as inhibitors of cyclooxygenase activity in whole cell cyclooxygenase assays. Both of these assays measure prostaglandin $E_2$ synthesis in response to arachidonic acid, using a radioimmunoassay. In these assays, 100% activity is defined as the difference between prostaglandin $E_2$ synthesis in the absence and presence of arachidonate.

Whole Cell Assays

For cyclooxygenase assays, osteosarcoma cells are cultured in 1 mL of media in 24-well multidishes (Nunclon) until confluent (1–2×10⁵ cells/well). U-937 cells are grown in spinner flasks and resuspended to a final density of 1.5×10⁶ cells/mL in 24-well multidishes (Nunclon). Following washing and resuspension of osteosarcoma and U-937 cells in 1 mL of HBSS, 1 μL of a DMSO solution of test compound or DMSO vehicle is added, and samples gently mixed. All assays are performed in triplicate. Samples are then incubated for 5 or 15 minutes at 37° C., prior to the addition of arachidonic acid. Arachidonic acid (peroxide-free, Cayman Chemical) is prepared as a 10 mM stock solution in ethanol and further diluted 10-fold in HBSS. An aliquot of 10 μL of this diluted solution is added to the cells to give a final arachidonic acid concentration of 10 μM. Control samples are incubated with ethanol vehicle instead of arachidonic acid. Samples are again gently mixed and incubated for a further 10 min. at 37° C. For osteosarcoma cells, reactions are then stopped by the addition of 100 μL of 1N HCl, with mixing and by the rapid removal of the solution from cell monolayers. For U-937 cells, reactions are stopped by the addition of 100 μL of 1N HCl, with mixing. Samples are then neutralized by the addition of 100 μL of 1N NaOH and $PGE_2$ levels measured by radioimmunoassay.

Whole cell assays for COX-2 and COX-1 using CHO transfected cell lines

Chinese hamster ovary (CHO) cell lines which have been stably transfected with an eukaryotic expression vector pCDNAIII containing either the human COX-1 or COX-2 cDNA's are used for the assay. These cell lines are referred to as CHO [hCOX-1] and CHO [hCOX-2], respectively. For cyclooxygenase assays, CHO[hCOX-1] cells from suspension cultures and CHO[hCOX-2] cells prepared by trypsinization of adherent cultures are harvested by centrifugation (300× g, 10 min) and washed once in HBSS containing 15 mM HEPES, pH 7.4, and resuspended in HBSS, 15 mM HEPES, pH 7.4, at a cell concentration of 1.5×10⁶ cells/ml. Drugs to be tested are dissolved in DMSO to 66.7-fold the highest test drug concentration. Compounds are typically tested at 8 concentrations in duplicate using serial 3-fold serial dilutions in DMSO of the highest drug concentration. Cells (0.3×10⁶ cells in 200 μl) are preincubated with 3 μl of the test drug or DMSO vehicle for 15 min at 37° C. Working solutions of peroxide-free AA (5.5 μM and 110 μM AA for the CHO [hCOX-1] and CHO [COX-2] assays, respectively) are prepared by a 10-fold dilution of a concentrated AA solution in ethanol into HBSS containing 15 mM HEPES, pH 7.4. Cells are then challenged in the presence or absence of drug with the AA/HBSS solution to yield a final concentration of 0.5 μM AA in the CHO[hCOX-1] assay and a final concentration of 10 μM AA in the CHO[hCOX-2] assay. The reaction is terminated by the addition of 10 μl 1N HCl followed by neutralization with 20 μl of 0.5N NaOH. The samples are centrifuged at 300× g at 4° C. for 10 min, and an aliquot of the clarified supernatant is appropriately diluted for the determination of $PGE_2$ levels using an enzyme-linked immunoassay for $PGE_2$ (Correlate $PGE_2$ enzyme immunoassay kit, Assay Designs, Inc.). Cyclooxygenase activity in the absence of test compounds is determined as the difference in $PGE_2$ levels of cells challenged with arachidonic acid versus the $PGE_2$ levels in cells mock-challenged with ethanol vehicle. Inhibition of $PGE_2$ synthesis by test compounds is calculated as a percentage of the activity in the presence of drug versus the activity in the positive control samples.

Assay of COX-1 Activity from U937 cell microsomes

U 937 cells are pelleted by centrifugation at 500× g for 5 min and washed once with phosphate-buffered saline and repelleted. Cells are resuspended in homogenization buffer consisting of 0.1M Tris-HCl, pH 7.4, 10 mM EDTA, 2 μg/ml leupeptin, 2 μg/ml soybean trypsin inhibitor, 2 μg/ml aprotinin and 1 mM phenyl methyl sulfonyl fluoride. The cell suspension is sonicated 4 times for 10 sec and is centrifuged at 10,000× g for 10 min at 4° C. The supernatant is centrifuged at 100,000× g for 1 hr at 4° C. The 100,000× g microsomal pellet is resuspended in 0.1M Tris-HCl, pH 7.4, 10 mM EDTA to approximately 7 mg protein/ml and stored at −80° C.

Microsomal preparations are thawed immediately prior to use, subjected to a brief sonication, and then diluted to a protein concentration of 125 μg/ml in 0.1M Tris-HCl buffer, pH 7.4 containing 10 mM EDTA, 0.5 mM phenol, 1 mM reduced glutathione and 1 μM hematin. Assays are performed in duplicate in a final volume of 250 μl. Initially, 5 μl of DMSO vehicle or drug in DMSO are added to 20 μl of 0.1M Tris-HCl buffer, pH 7.4 containing 10 mM EDTA in wells of a 96-deepwell polypropylene titre plate. 200 μl of the microsomal preparation are then added and pre-incubated for 15 min at room temperature before addition of 25 μl of 1M arachidonic acid in 0.1M Tris-HCl and 10 mM EDTA, pH 7.4. Samples are incubated for 40 min at room temperature and the reaction is stopped by the addition of 25 μl of 1N HCl. Samples are neutralized with 25 μl of 1N NaOH prior to quantitation of $PGE_2$ content by radioimmunoassay (Dupont-NEN or Amersham assay kits). Cyclooxygenase activity is defined as the difference between $PGE_2$ levels in samples incubated in the presence of arachidonic acid and ethanol vehicle.

Assay of the activity of purified human COX-2

The enzyme activity is measured using a chromogenic assay based on the oxidation of N,N,N',N'-tetramethyl-p-phenylenediamine (TMPD) during the reduction of $PGG_2$ to $PGH_2$ by COX-2 (Copeland et al. (1994) Proc. Natl. Acad. Sci. 91, 11202–11206).

Recombinant human COX-2 is purified from Sf9 cells as previously described (Percival et al (1994) Arch. Biochem. Biophys. 15, 111–118). The assay mixture (180 μL) contains 100 mM sodium phosphate, pH 6.5, 2 mM genapol X-100, 1 μM hematin, 1 mg/ml gelatin, 80–100 units of purified enzyme (One unit of enzyme is defined as the amount of enzyme required to produce an O.D. change of 0.001/min at 610 nm) and 4 μL of the test compound in DMSO. The mixture is pre-incubated at room temperature (22° C.) for 15 minutes prior to initiation of the enzymatic reaction by the addition of 20 μL of a sonicated solution of 1 mM arachidonic acid (AA) and 1 mM TMPD in assay buffer (without enzyme or hematin). The enzymatic activity is measured by estimation of the initial velocity of TMPD oxidation over the first 36 sec of the reaction. A non-specific rate of oxidation is observed in the absence of enzyme (0.007–0.010 O.D./min) and is subtracted before the calculation of the % inhibition. $IC_{50}$ values are derived from 4-parameter least squares non-linear regression analysis of the log-dose vs % inhibition plot.

HUMAN WHOLE BLOOD ASSAY

Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS, which induces COX-2. This assay can be used to evaluate the inhibitory effect of selective COX-2 inhibitors on $PGE_2$ production. As well, platelets in whole blood contain a large amount of the COX-1 enzyme. Immediately following blood clotting, platelets are activated through a thrombin-mediated mechanism. This reaction results in the production of thromboxane $B_2$ ($TxB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of $PGE_2$ after LPS induction (COX-2) and $TxB_2$ following blood clotting (COX-1) in the same assay.

Method

A. COX-2 (LPS-induced $PGE_2$ production)

Fresh blood is collected in heparinized tubes by venipuncture from both male and female volunteers. The subjects have no apparent inflammatory conditions and have not taken any NSAIDs for at least 7 days prior to blood collection. Plasma is immediately obtained from a 2 mL blood aliquot to use as blank (basal levels of $PGE_2$). The remaining blood is incubated with LPS (100 μg/ml final concentration, Sigma Chem, #L-2630 from *E. coli*; diluted in 0.1% BSA (Phosphate buffered saline) for 5 minutes at room temperature. Five hundred μL aliquots of blood are incubated with either 2 μL of vehicle (DMSO) or 2 μL of a test compound at final concentrations varying from 10 nM to 30 μM for 24 hours at 37° C. At the end of the incubation, the blood is centrifuged at 12,000× g for 5 minutes to obtain plasma. A 100 μL aliquot of plasma is mixed with 400 μL of methanol for protein precipitation. The supernatant is obtained and is assayed for $PGE_2$ using a radioimmunoassay kit (Amersham, RPA#530) after conversion of $PGE_2$ to its methyl oximate derivative according to the manufacturer's procedure.

B. COX-1 (Clotting-induced $TxB_2$ production)

Fresh blood is collected into vacutainers containing no anticoagulants. Aliquots of 50 μL are immediately transferred to siliconized microcentrifuge tubes preloaded with 2 μL of either DMSO or a test compound at final concentrations varying from 10 nM to 30 μM. The tubes are vortexed and incubated at 37° C. for 1 hour to allow blood to clot. At the end of incubation, serum is obtained by centrifugation (12,000× g for 5 min.). A 100 μL aliquot of serum is mixed with 400 μL of methanol for protein precipitation. The supernatant is obtained and is assayed for $TxB_2$ using a enzyme immunoassay kit (Cayman, #519031) according to the manufacturer's instruction.

RAT PAW EDEMA ASSAY

Protocol

Male Sprague-Dawley rats (150–200 g) are fasted overnight and are given, p0, either vehicle (1% methocel or 5% Tween 80) or a test compound. One hr later, a line is drawn using a permanent marker at the level above the ankle in one hind paw to define the area of the paw to be monitored. The paw volume ($V_O$) is measured using a plethysmometer (Ugo-Basile, Italy) based on the principle of water displacement. The animals are then injected subplantarly with 50 μl of 1% carrageenan solution in saline (FMC Corp, Me.) into the paw using an insulin syringe with a 25-gauge needle (i.e. 500 μg carrageenan per paw). Three hr later, the paw volume ($V_3$) is measured and the increases in paw volume ($V_3$- $V_O$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

NSAID-INDUCED GASTROPATHY IN RATS

Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}Cr$-labeled red blood cells from a donor rat. The animals are placed individually in metabolism cages with food and water ad lib. Feces are collected for a 48 h period and $^{51}Cr$ fecal excretion is calculated as a percent of total injected dose. $^{51}Cr$-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 Ci of sodium $^{51}$chromate for 30 min. at 37C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 Ci) is injected per rat.

PROTEIN-LOSING GASTROPATHY IN SQUIRREL MONKEYS

Rationale

Protein-losing gastropathy (manifested as appearance of circulating cells and plasma proteins in the GI tract) is a significant and dose-limiting adverse response to standard non-steroidal antiinflammatory drugs (NSAIDs). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}Cr$ (5 Ci/kg in 1 ml/kg phosphate buffer saline (PBS)) is administered 1 h after the last drug/vehicle dose, and feces collected for 24 h in a metabolism cage and assessed for excreted $^{51}Cr$ by gamma-counting. Venous blood is sampled 1 h and 8 h after the last drug dose, and plasma concentrations of drug measured by RP-HPLC.

RAT PLASMA LEVELS

Per Os Pharmacokinetics in Rats

Procedure

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box is firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.

Vehicles:

The following vehicles may be used in PO rat blood level determinations:

| | |
|---|---|
| PEG 200/300/400 - | restricted to 2 mL/kg |
| Methocel 0.5%–1.0% | 10 mL/kg |
| Tween 80 5% | 10 mL/kg |

Compounds for PO blood levels can be in suspension form. For better dissolution, the solution can be placed in a sonicator for approximately 5 minutes.

Intravenous Pharmacokinetics in Rats

Procedure

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they had lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone was removed. The time is noted. This constituted the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick to tail again.. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles:

The following vehicles may be used in IV rat blood level determinations:

Dextrose: 1 mL/kg

Molecusol 25%: 1 mL/kg

DMSO: (Dimethylsulfoxide) Restricted to a dose volume of 0.1 mL per animal

PEG 200: Not more than 60% mixed with 40% sterile water—1 mL/kg

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-1 8 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$Cl = \frac{DOSEiv \ (mg/kg)}{AUCiv}$$

The units of Cl are mL/h.kg (milliliters per hour kilogram)

Representative Biological Data

Compounds of the present invention are prodrugs of inhibitors of COX-2 and are thereby useful in the treatment of COX-2 mediated diseases as enumerated above. The extent of conversion of these compounds to the active COX-2 inhibitors may be seen in the representative results shown in Table III along with their antiinflammatory activity. The plasma levels indicated are the maximum rat plasma concentrations of the active COX-2 inhibitor observed when the rat was treated with a 20 mg/kg oral dose of the indicated prodrug. The $ED_{50}$ values in the rat paw edema assay represent the dose of prodrug required to reduce edema formation by 50% as compared to the vehicle control.

TABLE III

| Example | Plasma Levels ($\mu$M)* | Rat Paw Edema ($ED_{50}$, mg/kg) |
|---|---|---|
| 1 | 3.5 | 10 |
| 4 | 10 | 1.6 |
| 6 | 6 | 2.1 |

*Maximum plasma concentration of the corresponding carbonyl compound observed in rats when dosed at 20 mg/kg orally with the indicated prodrug.

The invention will now be illustrated by the following non-limiting examples in which, unless stated otherwise:

(i) all operations were carried out at room or ambient temperature, that is, at a temperature in the range 18–25° C.;

(ii) evaporation of solvent was carried out using a rotary evaporator underreduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and d' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta ($\delta$) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), M.P. (melting point), L (liter(s)), mL (milliliters), g (gram(s)), mg (milligrams (s)), mol (moles), mmol (millimoles), eq (equivalent(s)).

EXAMPLE 1

2-(3-Fluorophenyl)-4-methyl-3-(4-(methylsulfonyl)-phenyl)-2-(Z)-penten-1,4-diol

Step 1

5.5-Dimethyl-3-(3-fluorophenyl)-4-(4-methylthiophenyl)-5H-furanone

To a room temperature solution of 2-hydroxy-2-methyl-1-(4-methylthiophenyl)-propan-1-one (WO 95/00501, 20.0 g, 95.1 mmol), 3-fluorophenylacetic acid (29.3 g, 190 mmol) and DMAP (1.16 g, 9.5 mmol) in 500 mL of $CH_2Cl_2$ was added CMC (80.5 g, 190.2 mmol). The resulting mixture was stirred for 16 h under nitrogen. DBU (46 mL, 301 mmol) was then added, and the mixture stirred for 1.5 h. The reaction was quenched with 1M HCl, and the organic phase was washed with saturated aqueous $NaHCO_3$ and brine. The $CH_2Cl_2$ layer wa filtered through cotton and concentrated to give 50 g of the title compound, which was used in Step 2 without further purification.

Step 2

2-(3-Fluorophenyl)-4-methyl-3-(4-(methylthio)phenyl)-2-(Z)-penten-1,4-diol

To a −10° C. solution of 5,5-dimethyl-3-(3-fluorophenyl)-4-(4-methylthiophenyl)-5H-furanone (5.0 g, 15.2 mmol) in THF (45 mL) was added DIBAL (1.0M in THF, 22.8 mL) at a rate so as to maintain an internal temperature of less than 0° C. The resulting mixture was stirred at −5° C. for 15 min, then cooled to −20° C. LiAlH$_4$ (1.0M in THF, 30.4 mL) was added at a rate so as to maintain an internal temperature below −10° C. The mixture was then warmed to 5° C. for 16 h, then quenched cautiously with EtOAc, and partitioned between 1M tartaric acid and EtOAc. The organic phase was washed with saturated aqueous NaHCO$_3$ and brine, and dried over MgSO$_4$. Filtration and evaporation followed by an ether/hexane swish gave the 2.26 g of the title compound as a white solid.

Step 3
2-(3-Fluorophenyl-4-methyl-3 -(4-(methylsulfonyl)phenyl)-2-(Z)-penten-1,4-diol To a 0° C. solution of 2-(3-fluorophenyl)-4-methyl-3-(4-(methylthio)phenyl)-2-(Z)-penten-1,4-diol (Step 2, 100 mg, 0.30 mmol) in MeOH (3 mL) was added a solution of OXONE® (280 mg, 0.46 mmol) in water (1 mL). The reaction mixture was warmed to r.t. and stirred for 3 h, then diluted with saturated aqueous NaHCO$_3$(10 mL) and extracted with EtOAc. The organic phase was dried over Na$_2$SO$_4$ and concentrated to provide 80 mg of the title compound.

$^1$H NMR (400 MHz, CD$_3$COCD$_3$) ∂ 7.66 (2H, m), 7.27 (2H, m), 7.05 (1H, m), 6.77 (2H, m), 6.70 (1H, m), 4.75 (1H, s), 4.72 (2H, d), 4.03 (1H, t), 2.97 (3H, s), 1.39 (6H, s).

EXAMPLE 2
Acetic acid 4-acetoxy-2-(3-fluorophenyl)-4-methyl-3-(4-(methylsulfonyl)phenyl)-2-(Z)-pent-2-enyl ester To a solution of 2-(3-fluorophenyl)-4-methyl-3-(4-(methylsulfonyl)phenyl) 2-(Z)-penten-1,4-diol (Example 1, 150 mg, 0.4 mmol) in CH$_2$Cl$_2$ (10 mL) was added DMAP (100 mg), Et$_3$N (2 mL), and acetic anhydride (1 mL). The resulting mixture was stirred for 6 h, then quenched with MeOH (5 mL) and saturated aqueous NaHCO$_3$, then extracted with EtOAc. The organic phase was dried over MgSO$_4$ and concentrated to give 128 mg of the title compound as a white solid $^1$H NMR (400 MHz, CD$_3$COCD$_3$) ∂ 7.69 (2H, m), 7.46 (2H, m), 7.08 (1H, m), 6.74 (3H, m), 5.22 (2H, s), 2.98 (3H, s), 2.11 (3H, s), 1.83 (3H, s), 1.52 (6H, s).

EXAMPLE 3
2-(3-Fluorophenyl)-4-methoxy-4-methyl-3-((4-methylsulfonyl)phenyl)-2-(Z)-pentenoic acid Step 1
1-(t-Butyldimethylsilanolyl)-2-(3 -fluorophenyl)-4-methyl-3-(4-(methylthio)phenyl)-2-(Z)-penten-1-ol A mixture of 2-(3-fluorophenyl)-4-methyl-3-(4-(methylsulfonyl)phenyl)-2-(Z)-penten-1,4-diol (Example 1, Step 2, 2.20 g, 6.6 mmol), TBSCl (1.15 g, 7.6 mmol) and imidazole (1.08 g, 15.9 mmol) was dissolved in 10 mL of CH$_2$Cl$_2$ and stirred for 20 min. 2 mL of methanol was added, and 2 min later, the reaction was partitioned between CH$_2$Cl$_2$ and 1M HCl. The organic layer was washed with brine, filtered through cotton and evaporated to give 2.89 g of the title compound as a white solid.

Step 2
1-(t-Butyldimethyisilanolyl)-2-(3-fluorophenyl)-4-methoxy-4-methyl-3-(4-(methylthio)phenyl)-2-(Z)-pentene Sodium hydride (60% dispersion, 12.9 g, 323 mmol) was washed with hexane, dried and suspended in DMF. This suspension was added to a 0° C. solution of 1-(t-butyldimethylsilanolyl)-2-(3-fluorophenyl)-4-methyl-3-(4-(methylthio)phenyl)-2-(Z)-penten-1-ol (Step 1, 28.0 g, 64.7 mmol) and iodomethane (40 mL, 650 mmol) in 150 mL of DMF. After 1.5 h, the mixture was diluted with CH$_2$Cl$_2$ and poured slowly into a mixture of ice and 1M HCl. The organic layer was washed with 1M Na$_2$S$_2$O$_3$, 1M HCl (2×) and brine. The organic layer was filtered through cotton and concentrated to give 22 g of the title compound as a white solid.

Step 3
2-(3-Fluorophenyl)-4-methoxy-4-methyl-3-(4-(methylthio)phenyl)-2-(Z)-penten-1-ol To a 0° C. solution of 1-(t-butyldimethylsilanolyl)-2-(3-fluorophenyl)-4-methoxy-4-methyl-3-(4-(methylthio)phenyl)-2-(Z)-pentene (Step 2, 0.81 gm 1.8 mmol) was added TBAF (1.0M in THF, 2.0 mL), and the solution was a stirred at r.t. for 3.5 h. The mixture was then partitioned between CH$_2$Cl$_2$ and 1M HCl, and the organic phase was washed with brine, filtered through cotton and evaporated. The residue was purified by flash chromatography (45% EtOAc/Hex) to give 0.54 g of the title compound.

Step 4
2-(3-Fluorophenyl)-4-methoxy-4-methyl-3-(4-(methylsulfonyl)phenyl)-2-(Z)-penten-1-ol To a solution of 2-(3-fluorophenyl)-4-methoxy-4-methyl-3-(4-(methylthio)phenyl)-2-(Z)-penten-1-ol (Step 3, 0.54 g, 1.6 mmol) in 20 mL of 1:1 MeOH:CH$_2$Cl$_2$ was added MMPP (0.93 g, 1.9 mmol). After 2 h, the reaction mixture was concentrated then partitioned between CH$_2$Cl$_2$ and saturated aqueous NaHCO$_3$. The organic layer was washed with brine, filtered through cotton and concentrated to give 0.46 g of the title compound.

Step 5
2-(3-Fluorophenyl)-4-methoxy-4-methyl-3-(4-(methylsulfonyl)phenyl)-2-(Z)-pentenal to a −75° C. solution of oxalyl chloride (3.45 mL, 39.6 mmol) in CH$_2$Cl$_2$ (250 mL) was added DMSO (4.69 mL, 66.1 mmol) at a rate so as to maintain the internal temperature below −65° C. The resulting solution was stirred for 10 min, then a solution of 2-(3-fluorophenyl)-4-methoxy-4-methyl-3-(4-(methylsulfonyl)phenyl)-2-(Z)-penten-1-ol (Step 4, 5.00 g, 13.2 mmol) in CH$_2$Cl$_2$ (100 mL) was added via cannula. After 1 h at −75° C., triethylamine (20.3 mL, 145 mmol) was added and the mixture was warmed to −15 C for 15 min, then 0° C. for 30 min. The mixture was then partitioned between CH$_2$Cl$_2$ and 1M HCl. The organic phase was washed with brine, filtered through cotton and concentrated. The residue was swished with ether/hexane to provide 4.54 g of the title compound as a white solid.

Step 6
2-(3-Fluorophenyl)-4-methoxy-4-methyl-3-(4-(methylsulfonyl)phenyl)-2-(Z)-pentenoic acid To a suspension of 2-(3-fluorophenyl)-4-methoxy-4-methyl-3-(4-(methylsulfonyl)phenyl)-2-(Z)-pentenal (Step 5, 7.5 g, 20 mmol) in tBuOH (130 mL) was added 2-methyl-2-butene (30 mL) and a solution of sodium chlorite (16.7 g, 184 mmol) and NaH$_2$PO$_4$ (16.9 g, 140 mmol) in water (60 mL). After 1 h, the volatile components were remove in vacuo and the residue was partitioned between 1M HCl and CH$_2$Cl$_2$. The organic layer was washed with 1M Na$_2$S$_2$O$_3$, then 1M NaOH. The aqueous layer was acidified with 6M HCl and extracted with 10% EtOAc/CH$_2$Cl$_2$. The organic layer was washed with brine, filtered through cotton and concentrated to dryness. The residue was swished with ether to give 7.0 g of the title compound as a white solid.

$^1$H NMR (400 MHz, CD$_3$COCD$_3$) ∂ 11.07 (1H, br. s.), 7.78 (2H, m), 7.42 (2H, m), 7.14 (1H, m), 6.95 (2H, m), 6.85 (1H, m), 3.30 (3H, s), 3.02 (3H, s), 1.38 (6H, s).

A sample of the above compound (102 mg, 0.26 mmol) was dissolved in EtOH (10 mL) and treated with one equivalent of 1.00M NaOH (0.26 mL). The solution was evaporated, dissolved in water and freeze-dried to provide 113 mg of the corresponding sodium salt.

EXAMPLE 4

N,N-Dimethyl-2-(3-fluorophenyl)-4-methoxy-4-methyl-3-(4-(methylsulfonyl)phenyl)-2-(Z)-pentenamide To a suspension of 2-(3-fluorophenyl)-4-methoxy-4-methyl-3-(4-(methylsulfonyl)phenyl)-2-(Z)-pentenoic acid (Example 3, 1.00 g, 2.55 mmol) in $CH_2Cl_2$ (10 mL) was added triethylamine (0.89 mL, 6.37 mmol). The solution was cooled to −78° C. and HATU(0.97 g, 2.55 mmol) was added. The mixture was stirred for 30 min, then $Me_2NH$ was bubbled through for 30 sec., forming a thick suspension. $CH_2Cl_2$ (5 mL) was added to facilitate stirring, and the mixture was warmed to 0° C. over 2 h. After 3 h at 0° C., the mixture was partitioned between 1M HCl and $CH_2Cl_2$. The organic layer was washed with brine, filtered through cotton and concentrated. The residue was purified by flash chromatography followed by swishing in EtOAc/Hex to give 550 mg of the title compound.

$^1$H NMR (400 MHz, $CD_3COCD_3$) ∂ 7.75 (2H, br. s), 7.1 (2H, v. br. s), 7.05 (1H, m), 6.95 (2H, m), 6.75 (1H, m), 3.30 (3H, s), 3.00 (6H, s), 2.85 (3H, s), 1.43 (3H, s), 1.25 (3H, s).

EXAMPLE 5

N-(2-(Dimethylamino)ethyl)-N-methyl-2-(3-fluorophenyl)-4-methoxy-4-methyl-3-(4-(methylsulfonyl)phenyl)-2-(Z)-pentenamide To a −25° C. solution of 2-(3-fluorophenyl)-4-methoxy-4-methyl-3-(4-(methylsulfonyl)phenyl)-2-(Z)-pentenoic acid (Example 3, 0.50 g, 1.27 mmol) in $CH_2Cl_2$ (5 mL) was added triethylamine (1.77 mL, 12.7 mmol) and BOP (0.44 g, 1.27 mmol). After 10 min, N,N,N-trimethylethylenediamine (0.10 mL, 1.40 mmol) was added. After an additional 15 min, the reaction was warmed to r.t. and stirred 16 h. The resulting mixture was partitioned between 3M NaOH and $CH_2Cl_2$, and the organic layer was washed with brine, filtered through cotton and concentrated. The residue was purified by flash chromatography (1% $Et_3N$/5%MeOH/EtOAc) to provide 100 mg of the desired product.

$^1$H NMR (400 MHz, $CD_3COCD_3$) ∂ 7.75 (4H, br. m), 7.0 (1H, m), 6.92 (2H, m), 6.80 (1H, m), 3.50 (1H, m), 3.40 (1H, m), 3.25 (3H, m), 3.00 (3H, m), 2.55 (3H, s), 2.4 (2H, m), 2.15 (6H, m), 1.42 (3H, s), 1.25 (3H, m).

A sample of the above compound was dissolved in a minimal amount of MeOH and one equivalent of methanesulfonic acid was added. The solution was concentrated, then dissolved in water and freeze-dried to provide the corresponding methanesulfonate salt.

EXAMPLE 6

Methyl 2-(3-fluorophenyl)-4-methoxy-4-methyl-3-(4-(methylsulfonyl)phenyl)-2-(Z)-pentenoate To a suspension of 2-(3-fluorophenyl)-4-methoxy-4-methyl-3-(4-(methylsulfonyl)phenyl)-2-(Z)-pentenoic acid (Example 3, 0.15 g, 0.38 mmol) in $CH_2Cl_2$ (1.5 mL) was added an ethereal solution of diazomethane until a yellow colour persisted. The solvent was evaporated and the residue was swished in ether/hexane to give 121 mg of the desired product as a white solid.

$^1$H NMR (400 MHz, $CD_3COCD_3$) ∂ 7.45 (2H, m), 7.27 (2H, m), 7.15 (1H, m), 6.90 (2H, m), 6.85 (1H, m), 3.70 (3H, s), 3.25 (3H, s), 3.02 (3H, s), 1.35 (6H, s).

EXAMPLE 7

2-(3-Fluorophenyl)-4-methoxy-4-methyl-3-(4-(methylsulfonyl)phenyl)-2-(Z)-pentenamide To a −78° C. solution of 2-(3-fluorophenyl)-4-methoxy-4-methyl-3-(4-(methylsulfonyl)phenyl)-2-(Z)-pentenoic acid (Example 3, 0.40 g, 1.02 mmol) and $Et_3N$ (0.36 mL, 2.55 mmol) in $CH_2Cl_2$ (10 mL) was added HATU (0.39 g, 1.02 mmol). After 35 min, $NH_3$ was bubbled through the solution, forming a slurry. The mixture was allowed to warm to r.t. over 2 h, then was partitioned between EtOAc and 1M HCl. The organic layer was washed with 1M NaOH and brine, dried over $MgSO_4$, and concentrated. The residue was purified by flash chromatography (35% acetone/toluene) to give 16 mg of the title compound.

$^1$H NMR (400 MHz, $CD_3COCD_3$) ∂ 7.75 (2H, m), 7.35 (2H, m), 7.05 (1H, m), 6.95 (2H, m), 6.25 (1H, m), 6.40 (2H, br. s), 3.32 (3H, s), 3.00 (3H, s), 1.37 (6H, s).

EXAMPLE 8

N-(2(2-(2-(2-(2-(2-Aminoethoxy)-ethoxy)-ethoxy)-ethoxy)-ethoxy)-ethoxy)-ethyl)-2-(3-fluorophenyl)-4-methoxy-4-methyl-3-(4-(methylsulfonyl)phenyl)-2-(Z)-pentenamide Step 1

1-Chloro-2-(2-(2-(2-(2-(2-chloroethoxy)-ethoxy)-ethoxy)-ethoxy)-ethoxy)-ethane

To hexaethylene glycol (4.0 mL, 16 mmol) was added thionyl chloride (9.3 mL, 128 mmol). The solution was heated to reflux for 16 h. The mixture was concentrated to dryness to give 5.12 g of the title compound as a light red oil.

Step 2

(2-(2-(2-(2-(2-(2-Aminoethoxy)-ethoxy)-ethoxy)-ethoxy)-ethoxy)-ethyl amine

A mixture of 1-chloro-2-(2-(2-(2-(2-(2-chloroethoxy)-ethoxy)-ethoxy)-ethoxy)-ethoxy)-ethane (Step 1, 0.80 g, 2.5 mmol), 30% $NH_4OH$ (25 mL) and water (7.5 mL) was sealed in a tube and heated to 60° C. for five days. The reaction was cooled and sodium carbonate (8 g) was added. The solution was extracted with five portions of $CH_2Cl_2$. The combined organic extracts were washed with brine, filtered through cotton and concentrated to give 0.50 g of the title compound.

Step 3

N-(2-(2-(2-(2-(2-(2-Aminoethoxy)-ethoxy)-ethoxy)-ethoxy)-ethoxy)-ethoxy)-ethyl)-2-(3-fluorophenyl)-4-methoxy-4-methyl-3-(4-(methylsulfonyl)phenyl)-2-(Z)-pentenamide To a −78° C. solution of 2-(3-fluorophenyl)-4-methoxy-4-methyl-3-(4-(methylsulfonyl)phenyl)-2-(Z)-pentenoic acid (Example 3, 0.35 g, 0.89 mmol) and $Et_3N$ (0.31 mL, 2.23 mmol) in $CH_2Cl_2$ (4 mL) was added HATU (0.34 g, 0.89 mmol). After 30 min, a solution of (2-(2-(2-(2-(2-(2-aminoethoxy)-ethoxy)-ethoxy)-ethoxy)-ethoxy)-ethyl amine (Step 2, 0.50 g, 1.78 mmol) in $CH_2Cl_2$ (1 mL) was added and the reaction mixture was allowed to warm to r.t. over 2 h. The mixture was partitioned between 1M NaOH and $CH_2Cl_2$. the organic layer was washed with brine, filtered through cotton and concentrated. The residue was purified by flash chromatography (10% MeOH/$CH_2Cl_2$) to give 100 mg of product contaminated with tetramethylurea. This material was dissolved in $CH_3CN$ and washed with hexane (4×) to provide 20 mg of the title compound.

$^1$H NMR (400 MHz, $CD_3COCD_3$) ∂ 7.72 (2H, m), 7.38 (4H, m), 7.05 (1H, m), 6.95 (2H, m), 6.75 (1H, m), 3.7-3.4 (21H, m), 3.37 (3H, m), 3.32 (3H, s), 3.00 (3H, s), 2.84 (1H, m), 1.32 (6H, m).

STARTING MATERIALS

The following section provides example for the preparation of starting materials for the preparation of compounds within the scope of the invention. As appreciated by those of skill in the art, the following section is a self-contained unit. Thus, while the section may contain Example numbers and other designations which duplicate those used for the compounds of the instant invention, such duplication is not to be regarded as an assertion that the Examples and designations are identical.

Starting materials for the preparation of compounds of the present invention can be prepared according to the following methods. The substituents in these methods have the following definitions unless indicated otherwise, and, as one who is familiar with the art will be aware, insofar as they are compatible with the chemistry described:

X is selected from the group consisting of
(a) $CH_2$,
(b) CHOH,
(c) CO,
(d) O,
(e) S, and
(f) $N(R^{15})$,
with the proviso that when $R^3$ and $R^4$ are other than
(1) both hydrogen, or
(2) both $C_{1-10}$ alkyl, or
(3) joined together with the carbon to which they are attached form a saturated monocyclic carbon ring of 3, 4, 5, 6 or 7 atoms,
then
X is selected from CO, O, S or $N(R^{15})$;

$R^1$ is selected from the group consisting of
(a) $SO_2CH_3$,
(b) $SO_2NR^{16}R^{17}$,
(c) $SO_2NHC(O)CF_3$,
(d) $S(O)(NH)NH_2$,
(e) $S(O)(NH)NHC(O)CF_3$,
(f) $P(O)(CH_3)NH_2$, and
(g) $P(O)(CH_3)_2$, $R^2$ is selected from the group consisting of
(a) $C_{1-10}$alkyl,
(b) mono-, di- or tri-substituted phenyl or naphthyl wherein the substituents are selected from the group consisting of
(1) hydrogen,
(2) halo,
(3) $C_{1-10}$alkoxy,
(4) $C_{1-10}$alkyltio,
(5) CN,
(6) $C_{1-6}$ fluoroalkyl
(7) $C_{1-10}$ alkyl,
(8) $N_3$,
(9) —$CO_2H$,
(10) —$CO_2$—$C_{1-10}$alkyl,
(11) —$C(R^5)(R^6)$—OH,
(12) —$C(R^5)(R^6)$—O—$C_{1-4}$alkyl, and
(13) —$C_{1-6}$alkyl—$CO_2$—$R^5$,
(14) benzyloxy,
(15) —O—($C_{1-6}$alkyl)—$CO_2R^5$, and
(16) —O—($C_{1-6}$alkyl)—$NR^5R^6$,
(c) mono- , di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2, or 3 additional N atoms, wherein the substituents are selected from the group consisting of
(1) hydrogen,
(2) halo,
(3) $C_{1-10}$alkyl,
(4) $C_{1-10}$alkoxy,
(5) $C_{1-10}$alkylthio,
(6) CN,
(7) $CF_3$,
(8) $N_3$,
(9) —$C(R^5)(R^6)$—OH,
(10) —$C(R^5)(R^6)$—O—$C_{1-10}$alkyl, and
(11) $C_{1-6}$fluoroalkyl;
(d) a mono- or di- substituted benzoheterocycle in which the heterocycle is a 5, 6, or 7-membered ring which may contain 1 or 2 heteroatoms chosen independently from O, S, or N and which may contain a carbonyl group or a sulfonyl group; wherein the substituents are selected from the group consisting of
(1) hydrogen,
(2) halo,
(3) $C_{1-10}$alkyl,
(4) $C_{1-10}$alkoxy,
(5) $C_{1-10}$alkylthio,
(6) CN,
(7) $CF_3$,
(8) $N_3$,
(9) —$C(R^5)(R^6)$—OH,
(10) —$C(R^5)(R^6)$—O—$C_{1-10}$alkyl, and
(11) $C_{1-6}$fluoroalkyl;
(e) a heterocycloalkyl group of 5, 6 or 7 members which contains 1 or 2 heteroatoms chosen from O, S, or N and optionally contains a carbonyl group or a sulfonyl group.
(f) a mono- or di- substituted benzocarbocycle in which the carbocycle is a 5, 6, or 7-membered ring which optionally contains a carbonyl group, wherein the substituents are selected from the group consisting of
(1) hydrogen,
(2) halo,
(3) $C_{1-10}$alkyl,
(4) $C_{1-10}$alkoxy,
(5) $C_{1-10}$alkylthio,
(6) CN,
(7) $CF_3$,
(8) $N_3$,
(9) —$C(R^5)(R^6)$—OH,
(10) —$C(R^5)(R^6)$—O—$C_{1-10}$alkyl, and
(11) $C_{1-6}$fluoroalkyl;
(g) a mono- or di-substituted bicyclic heteroaryl of 8, 9, or 10 members, containing 2 to 5 heteroatoms chosen independently from O, S or N, and in which each ring contains at least one heteroatom, wherein the substituents are selected from the group consisting of
(1) hydrogen,
(2) halo,
(3) $C_{1-10}$alkyl,
(4) $C_{1-10}$alkoxy,
(5) $C_{1-10}$alkyltio,
(6) CN,
(7) $CF_3$,
(8) $N_3$,
(9) —$C(R^5)(R^6)$—OH,
(10) —$C(R^5)(R^6)$—O—$C_{1-10}$alkyl, and
(11) $C_{1-6}$fluoroalkyl;

$R^3$ is hydrogen, $C_{1-10}$ alkyl, $CH_2OR^7$, CN, $CH_2CN$, $C_{1-6}$fluoroalkyl, F, $CON(R^7)2$, mono- or di-substituted phenyl, mono or di-substituted benzyl, mono- or di-substituted heteroaryl, mono or di-substituted heteroarylmethyl, wherein the substituents are selected from the group consisting of
(1) hydrogen,
(2) halo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$—OH,
(10) —$C(R^5)(R^6)$—O—$C_{1-4}$alkyl, and
(11) $C_{1-6}$fluoroalkyl;
$R^4$ is
(a) hydrogen
(b) $C_{1-10}$alkyl,
(c) $C_{1-10}$alkoxy,
(d) $C_{1-10}$alkylthio,
(e) —OH,
(f) —$OCOR^7$,
(g) —SH,
(h) —$SCOR^7$,
(i) —$OCO_2R^8$,
(j) —$SCO_2R^8$,
(k) $OCON(R^7)_2$,
(l) $SCON(R^7)_2$, and
(m) $C_{1-6}$fluoroalkyl;
or $R^3$ and R4 together with the carbon to which they are attached form a saturated monocyclic carbon ring of 3, 4, 5, 6 or 7 atoms;
$R^5$ and $R^6$ are each independently selected from the group consisting of
(a) hydrogen, and
(b) $C_{1-10}$alkyl,
or $R^5$ and $R^6$ together with the atom to which they are attached form a saturated monocyclic ring of 3, 4, 5, 6 or 7 atoms;
each $R^7$ is independently selected from the group consisting of
(a) hydrogen,
(b) $C_{1-6}$alkyl,
(c) phenyl or monosubstituted phenyl wherein the substituents may be halo, $C_{1-6}$alkyl, $C_{1-6}$alkoxy, $C_{1-6}$alkylthio, CN, or $CF_3$, and
(d) benzyl or monosubstituted benzyl wherein the substituents may be halo, $C_{1-6}$alkyl, $C_{1-6}$alkoxy, $C_{1-6}$alkylthio, CN, or $CF_3$, or
two R7 groups taken together with the nitrogen to which they are attached form a saturated monocyclic ring of 5, 6 or 7 atoms, optionally containing an additional O, S or NR5;
each $R^8$ is independently selected from the group consisting of
(a) $C_{1-6}$alkyl,
(b) phenyl or monosubstituted phenyl wherein the substituents may be halo, $C_{1-6}$alkyl, $C_{1-6}$alkoxy, $C_{1-6}$alkylthio, CN, or $CF_3$, and
(c) benzyl or monosubstituted benzyl wherein the substituents may be halo, $C_{1-6}$alkyl, $C_{1-6}$alkoxy, $C_{1-6}$alkylthio, CN, or $CF_3$;

$R^9$ and $R^{10}$ are independently selected from the group consisting of:
(a) hydrogen, and
(b) $C_{1-7}$alkyl, or
$R^9$ and $R^{10}$ together with the carbon atom to which they are attached form a carbonyl or thiocarbonyl group;
$R^{11}$ and $R^{12}$ are independently
(a) hydrogen,
(b) mono- or di-substituted phenyl or mono- or di-substituted benzyl or mono- or di-substituted heteroaryl or mono- or di-substituted heteroarylmethyl, wherein the substituents are selected from the group consisting of
(1) hydrogen,
(2) fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^{13})(R^{14})$—OH,
(10) —$C(R^{13})(R^{14})$—O—$C_{1-4}$alkyl, and
(11) $C_{1-6}$fluoroalkyl, or
(c) $C_{1-7}$alkyl, $CH_2OR^7$, CN, $CH_2CN$, $C_{1-6}$fluoroalkyl, $CON(R^7)_2$, F, or $OR^7$; or
$R^{11}$ and $R^{12}$ together with the carbon to which they are attached form a saturated monocyclic carbon ring of 3, 4, 5, 6 or 7 atoms;
$R^{13}$ and $R^{14}$ are independently selected from the group consisting of:
(a) hydrogen,
(b) $C_{1-7}$alkyl, or
$R^{13}$ and $R^{14}$ together with the carbon to which they are attached form a carbonyl, —C(=S)—, or a saturated monocyclic carbon ring of 3, 4, 5, 6, or 7 atoms.
$R^{15}$ is selected from the group consisting of:
(a) hydrogen,
(b) $C_{1-10}$alkyl,
(c) mono-, di- or tri-substituted phenyl or naphthyl wherein the substituents are selected from the group consisting of
(1) hydrogen,
(2) halo,
(3) $C_{1-10}$alkoxy,
(4) $C_{1-10}$alkylthio,
(5) CN,
(6) $C_{1-6}$fluoroalkyl
(7) $C_{1-10}$alkyl,
(8) $N_3$,
(9) —$CO_2H$,
(10) —$CO_2$—$C_{1-10}$alkyl,
(11) —$C(R^5)(R^6)$—OH,
(12) —$C(R^5)(R^6)$—O—$C_{1-4}$alkyl, and
(13) —$C_{1-6}$alkyl—$CO_2$—$R^5$;
(14) benzyloxy,
(15) —O—$(C_{1-6}$alkyl)—$CO_2R^5$, and
(16) —O—$(C_{1-6}$alkyl)—$NR^5R^6$,
(d) mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or
the heteroaryl is a monocyclic ring of 6 atoms, said ring having one hetero atom which is N, and optionally 1, 2, or 3 additional N atoms, wherein the substituents are selected from the group consisting of (1) hydrogen,
(2) halo,
(3) $C_{1-10}$alkyl,
(4) $C_{1-10}$alkoxy,
(5) $C_{1-10}$alkylthio,
(6) CN,
(7) $CF_3$,
(8) $N_3$,
(9) —$C(R^5)(R^6)$—OH,
(10) —$C(R^5)(R^6)$—O—$C_{1-10}$alkyl, and
(11) $C_{1-6}$fluoroalkyl;
(e) a mono- or di- substituted benzoheterocycle in which the heterocycle is a 5, 6, or 7-membered ring which may contain 1 or 2 heteroatoms chosen independently from O, S, or N and which may contain a carbonyl group or a sulfonyl group; wherein the substituents are selected from the group consisting of
(1) hydrogen,
(2) halo,
(3) $C_{1-10}$alkyl,
(4) $C_{1-10}$alkoxy,
(5) $C_{1-10}$alkylthio,
(6) CN,
(7) $CF_3$,
(8) $N_3$,
(9) —$C(R^5)(R^6)$—OH,
(10) —$C(R^5)(R^6)$—O—$C_{1-10}$alkyl, and
(11) $C_{1-6}$fluoroalkyl;
(f) a heterocycloalkyl group of 5, 6 or 7 members which contains 1 or 2 heteroatoms chosen from O, S, or N and optionally contains a carbonyl group or a sulfonyl group.
(g) a mono- or di- substituted benzocarbocycle in which the carbocycle is a 5, 6, or 7-membered ring which optionally contains a carbonyl group, wherein the substituents are selected from the group consisting of
(1) hydrogen,
(2) halo,
(3) $C_{1-10}$alkyl,
(4) $C_{1-10}$alkoxy,
(5) $C_{1-10}$alkylthio,
(6) CN,
(7) $CF_3$,
(8) $N_3$,
(9) —$C(R^5)(R^6)$—OH,
(10) —$C(R^5)(R^6)$—O—$C_{1-4}$alkyl, and
(11) $C_{1-6}$fluoroalkyl;
$R^{16}$ and $R^{17}$ are independently selected from the group consisting of
(a) hydrogen
(b) $C_{1-10}$alkyl,
(c) $C_{1-10}$alkanoic acid,
(d) $C_{1-10}$alkylamine,
(e) phenyl or monosubstituted phenyl wherein the substituents are halo, $C_{1-10}$alkyl, $C_{1-10}$alkoxy, $C_{1-10}$alkylthio, $C_{1-10}$alkanoic acid, $C_{1-10}$alkylamine, CN, $CO_2H$ or $CF_3$, and
(f) benzyl or monosubstituted benzyl wherein the substituents are halo, $C_{1-10}$alkyl, $C_{1-10}$alkoxy, $C_{1-10}$alkylthio, $C_{1-10}$alkanoic acid, $C_{1-10}$alkylamine, CN, COOH or $CF_3$, or
R16 and R17 together with the nitrogen to which they are attached form a saturated monocyclic ring of 5, 6 or 7 atoms, optionally containing an additional O, S or $NR^5$.
For purposes of this specification heteroaryl as in $R^2$, $R^3$, or $R^{15}$ is intended to include, but is not limited to optionally mono- or di-substituted (1) furanyl,
(2) diazinyl,
(3) imidazolyl,
(4) isooxazolyl,
(5) isothiazolyl,
(6) oxadiazolyl,
(7) oxazolyl,
(8) pyrazolyl,
(9) pyridyl,
(10) pyrrolyl,
(11) tetrazinyl
(12) tetrazolyl.
(13) thiadiazolyl,
(14) thiazolyl,
(15) thienyl,
(16) triazinyl, or
(17) triazolyl.

Similarly, for purposes of this specification cyclic groups such as a heterocycloalkyl or benzocarbocycle or benzoheterocycle such as in $R^2$ or $R^{15}$ is intended to include, but is not limited to optionally mono- or di-substituted (1) tetrahydrothiopyranyl,
(2) thiomorpholinyl,
(3) pyrrolidinyl,
(4) hexahydroazepinyl,
(5) indanyl,
(6) tetralinyl,
(7) indolyl,
(8) benzofuranyl,
(9) benzothienyl,
(10) benzimidazolyl,
(11) benzothiazolyl,

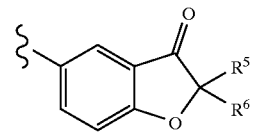

(12)

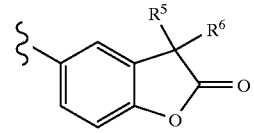

(13)

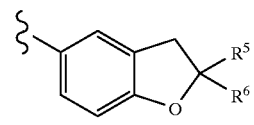

(14)

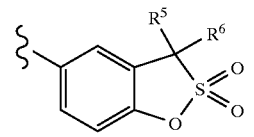

(15)

(16) 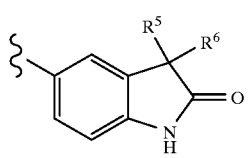
(17) 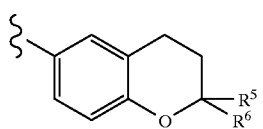
(18) 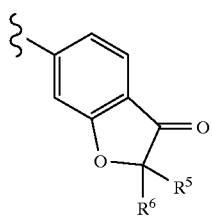
(19) 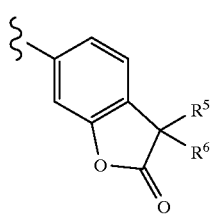
(20) 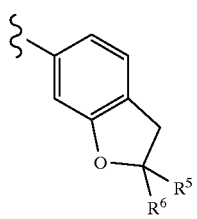
(21) 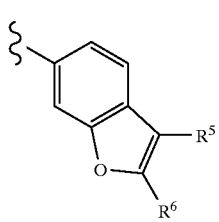
(22) 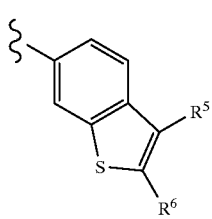
(23) 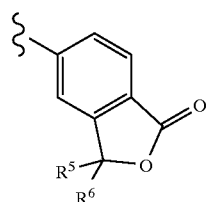
(24) 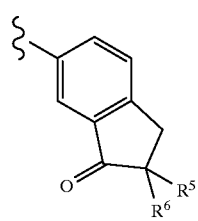
(25) 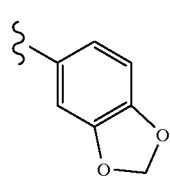
(26) 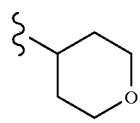
(27) 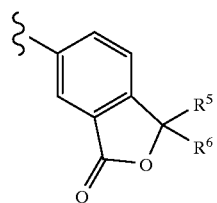
(28) 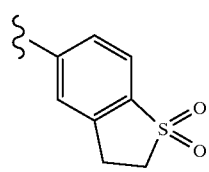
(29) 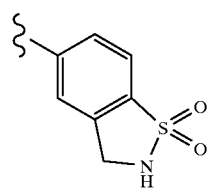

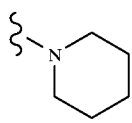 (30)
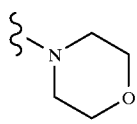 (31)
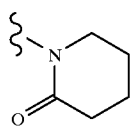 (32)
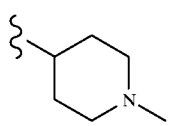 (33)
Similarly, for purposes of this specification bicyclic heteroaryl as in R² is intended to include, but is not limited to optionally mono- or di-substituted
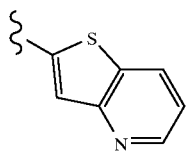 (1)
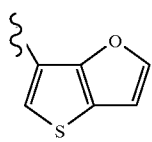 (2)
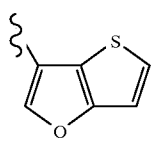 (3)
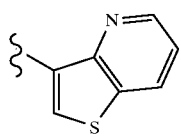 (4)
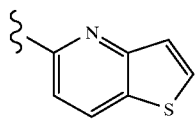 (5)
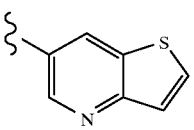 (6)
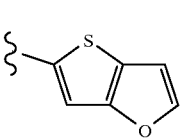 (7)
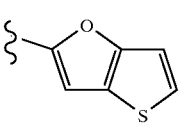 (8)
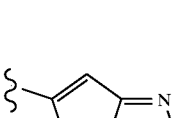 (9)
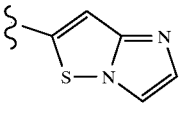 (10)
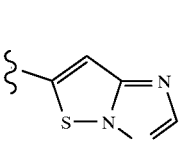 (11)
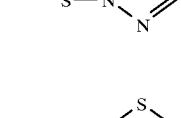 (12)
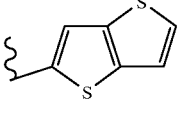 (13)
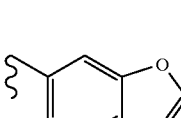 (14)
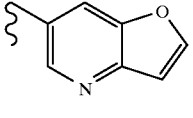 (15)

(16) 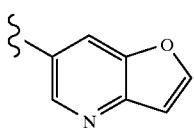

(17) 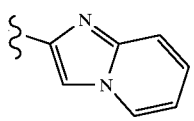

(18) 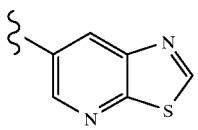

(19) 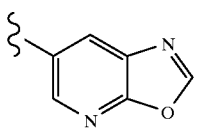

(20) 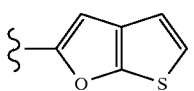

(21) 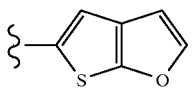

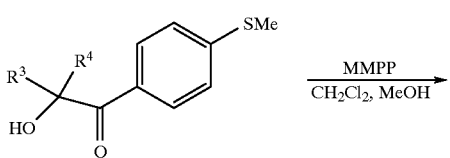

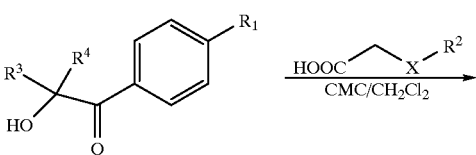

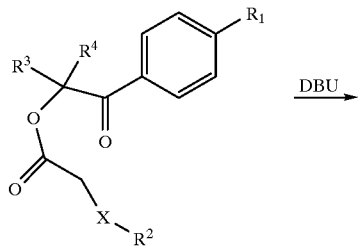

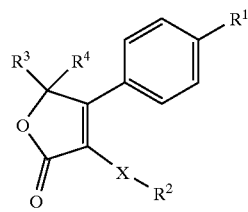

Ia  $R^1 = SO_2Me$

Method A

An appropriately substituted acid halide is reacted with thioanisole in a solvent such as chloroform in the presence of a Lewis acid such as aluminum chloride to afford a ketone which is then hydroxylated with base such as aqueous sodium hydroxide in a solvent such as carbon tetrachloride with a phase transfer agent such as Aliquat 336. Then treatment with an oxidizing agent such as MMPP in solvents such as $CH_2Cl_2/MeOH$, affords an sulfone which is reacted with an appropriately substituted acetic acid in a solvent such as $CH_2Cl_2$ in the presence of an esterifying agent such as CMC and DMAP and then treated with DBU to afford lactone Ia.

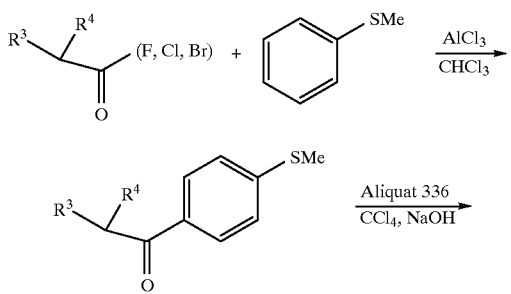

Method B

An appropriately substituted hydroxyketone is acylated within appropriately substituted acid halide in a solvent such as dichloromethane in the presence of a base such as pyridine. The ester obtained is then reacted with an appropriately substituted nucleophile $R^2XH$ in a solvent such as DMF and with a base such as sodium hydride, then treatment with DBU in a solvent such as acetonitrile affords lactone Ia.

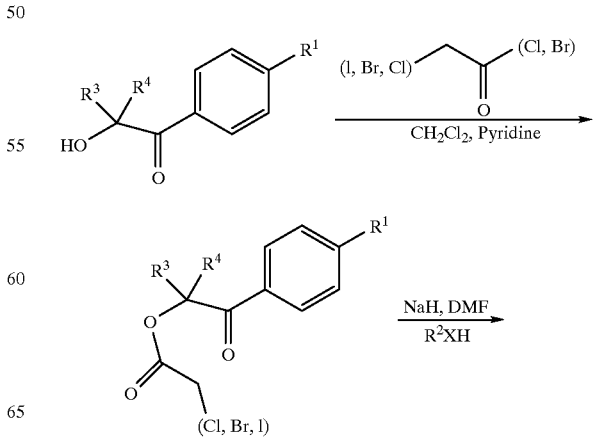

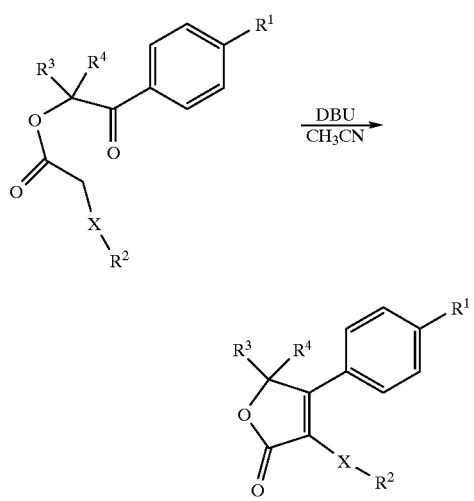

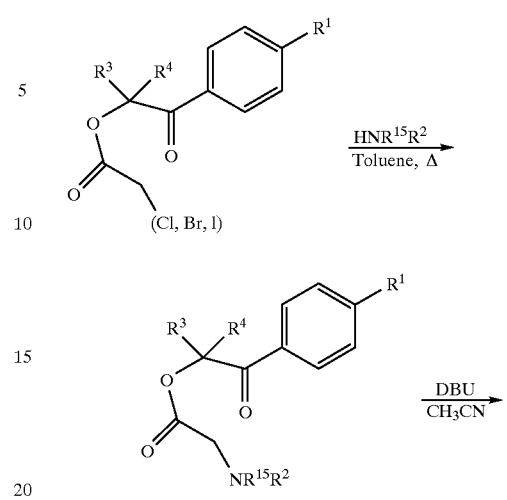

Ia  $R^1 = SO_2Me$
      $X = O, S, NR^{15}$

Ia  $X = NR^{15}$

Method C

A halo ester of acetic acid is coupled with an appropriately substituted nucleophile in water with sodium hydroxide to give an appropriately substituted acetic acid which is then reacted as in method A to afford lactone Ia.

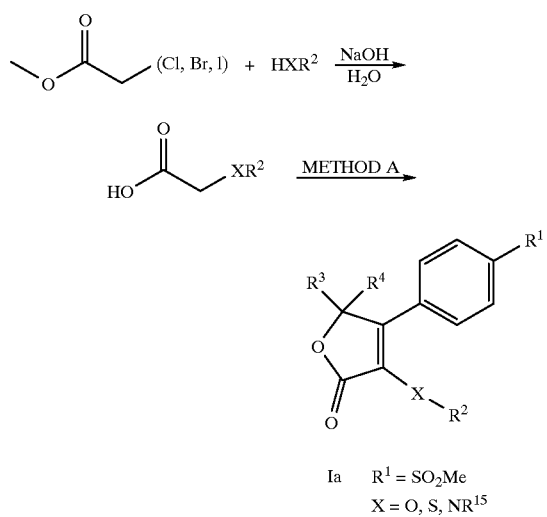

Ia  $R^1 = SO_2Me$
      $X = O, S, NR^{15}$

Method D

A halo ester is reacted with an appropriately substituted amine $R^2R^{15}NH$ in a solvent such as toluene to give an intermediate which is then reacted with DBU in a solvent such as acetonitrile to afford lactone Ia.

Method E

An appropriately substituted bromoketone is reacted with an appropriately substituted acid in a solvent such as ethanol or acetonitrile in the presence of a base such as diisopropylethylamine or triethylamine to afford an ester which is then treated with DBU in a solvent such as acetonitrile to afford lactone Ia.

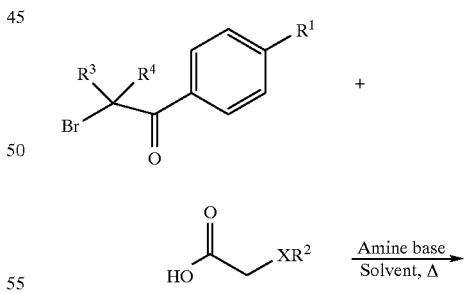

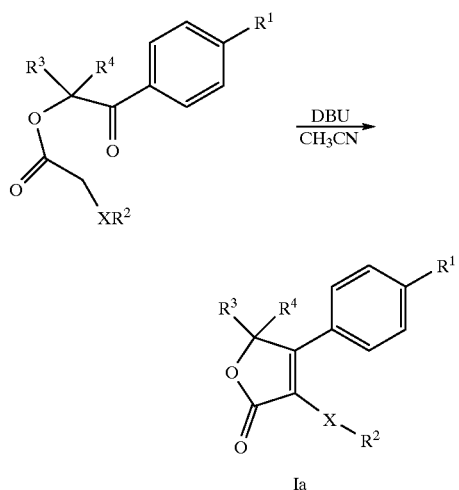

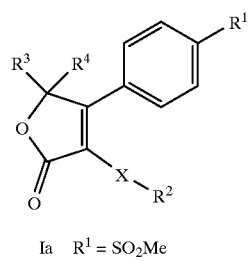

Ia  R¹ = SO₂Me

Method G

An appropriately substituted hydroxyketone is acylated with acetyl bromide or chloride in a solvent such as dichloromethane with a base such as DBU and DMAP. Further treatment with a base such as sodium hydride in a solvent such as DMF effects cyclization to afford the 5-membered lactone. Treatment of this lactone with a base such as LDA and an appropriately substituted acid halide in a solvent such as THF, followed by oxidation with a reagent such as MMPP in solvent such as $CH_2Cl_2$/MeOH and hydrolysis by a base such as NaOH in a solvent such as MeOH/THF gives an alcohol Ib which is then oxidized to lactone Ic by a reagent such as Jone's reagent in a solvent such as acetone(the initially formed ketone is reduced in the reaction and acylated, thus requiring hydrolysis and re-oxidation to obtain ketone Ic). Alternatively, alcohol Ib can be obtained by using an aldehyde $R^2CHO$ as the electrophile instead of an acid halide.

Method F

An appropriately substituted hydroxyketone is reacted with an appropriately substituted acid halide in a solvent such as dichloromethane and with a base such as pyridine to afford an ester which is then cyclized using sodium hydride in a mixture of THF and DMF to afford a lactone. The lactone is then oxidized with an oxidizing agent such as MMPP, mCPBA or OXONE® in solvents such as dichloromethane and/or methanol to afford lactone Ia.

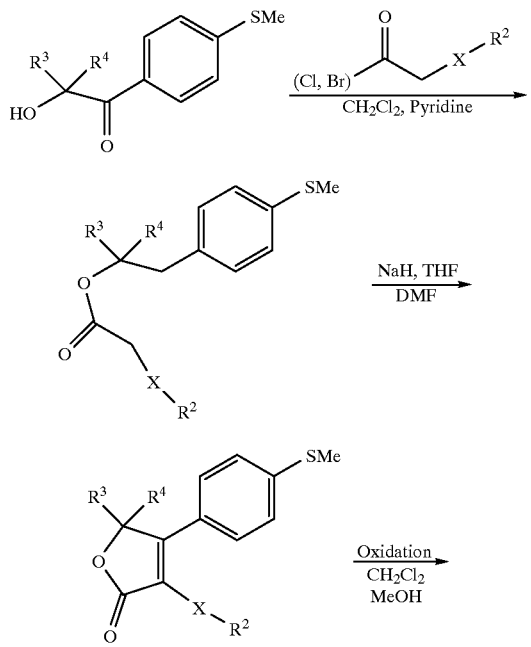

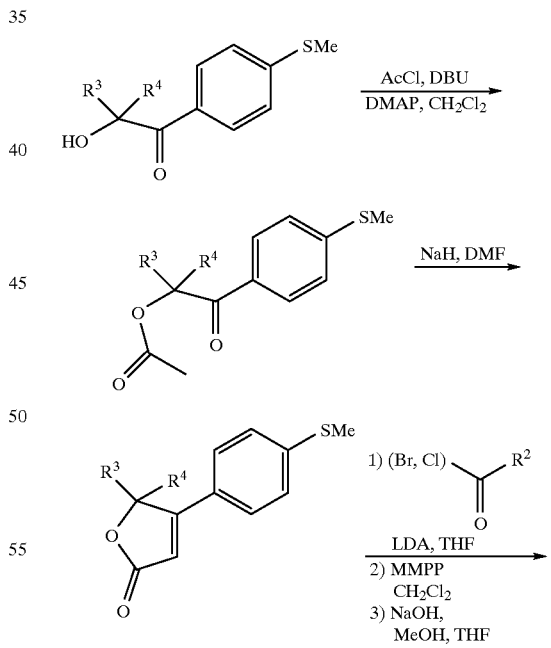

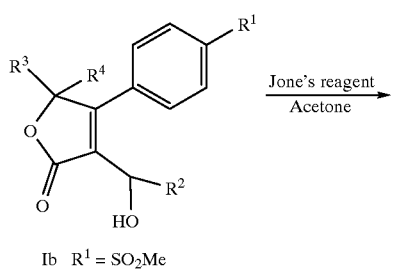

Ib  R$^1$ = SO$_2$Me

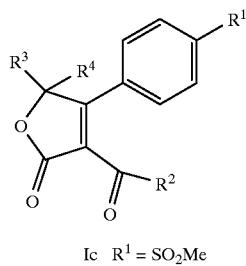

Ic  R$^1$ = SO$_2$Me

Method H

An appropriately substituted methyl sulfide is oxidized to the sulfoxide with a reagent such as MMPP in solvents such as dichloromethane and methanol followed by treatment with trifluoroacetic anhydride, then aqueous sodium hydroxide. Further treatment by Cl$_2$ in aqueous acetic acid followed by treatment by an amine affords an intermediate sulfonamide. This sulfonamide is then esterified with an appropriately substituted acid in the presence of a reagent such as CMC and further treatment with a base such as DBU affords the lactone. In the case where the amine group is protected by an acid labile group treatment with an acid such as trifluoroacetic acid in a solvent such as dichloromethane affords compound Ia.

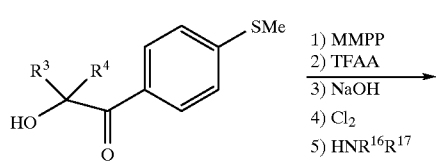

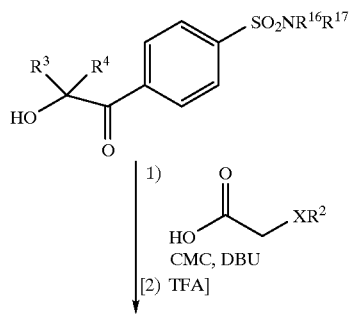

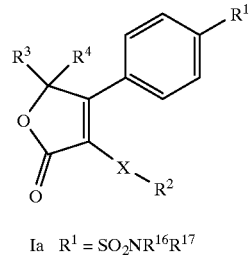

Ia  R$^1$ = SO$_2$NR$^{16}$R$^{17}$

Method I

An appropriately substituted bromoketone is reacted with an appropriately substituted acid in a solvent such as acetonitrile and with a base such as Et$_3$N. Treatment with DBU and then O$_2$ gives a hydroxy compound Id. Etherification of this hydroxy with an alcohol in a solvent such as THF and with an acid such HCl gives Ie. By oxidation of the sulfide into a sulfone by a reagent such as m-CPBA and then displacement of this sulfone by an appropriately substituted nucleophile compound If is obtained.

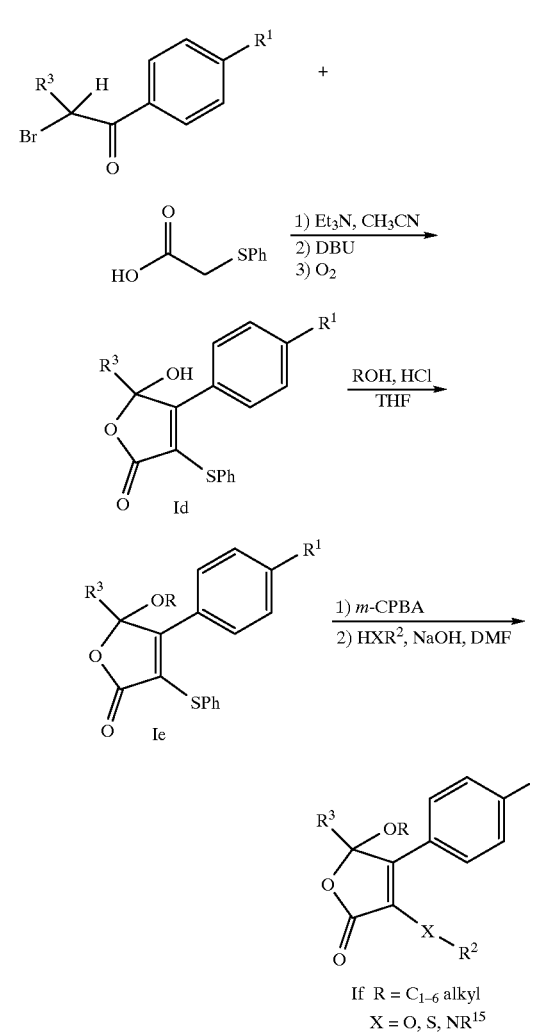

If  R = C$_{1-6}$ alkyl
X = O, S, NR$^{15}$

Method J

An appropriately substituted nucleophile is reacted with an appropriately substituted haloacetate in a solvent such as acetonitrile with a base such as DBU to afford compound Ia.

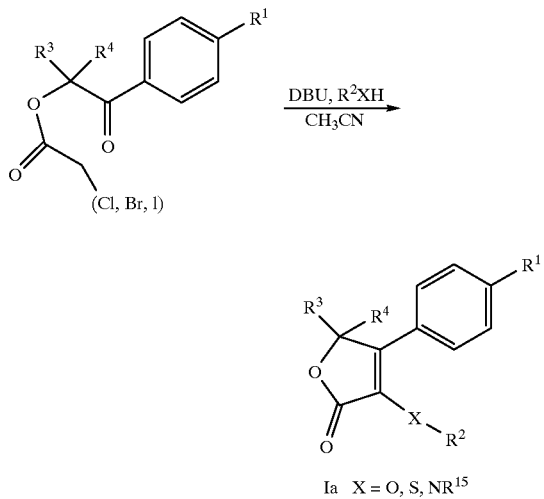

Ia X = O, S, $NR^{15}$

Method K

An appropriately substituted vinyl ketone is coupled with an appropriately substituted benzaldehyde with a catalyst such as 3-benzyl-5-(2-hydroxyethyl)-4-methylthiazolium chloride in the presence of a base such as triethylamine in a solvent such as 1,4-dioxane to form a diketone. The diketone is cyclized in a solvent such as methanol with a base such as DBU to the final product Ig. When $R^1$=$SO_2Me$, the starting material can also be a p-methylthiobenzaldehyde, with the methylthio group being oxidized to $SO_2Me$ using MMPP, mCPBA or OXONE® in the last step.

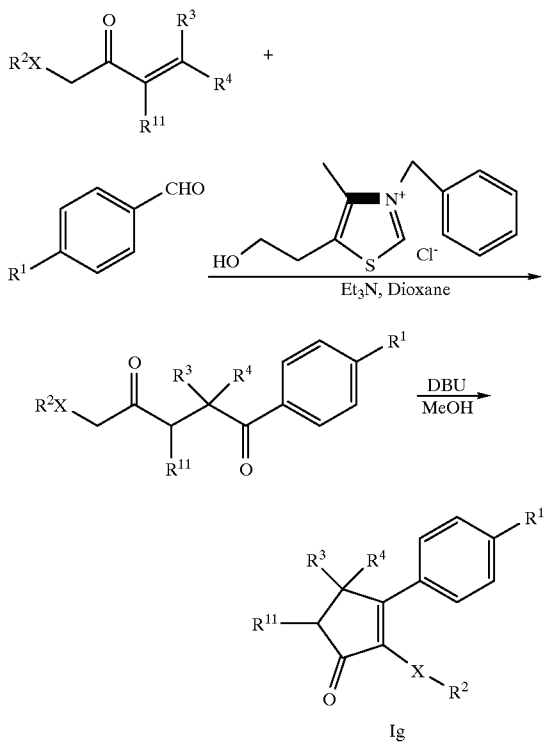

EXAMPLE 1

3-(3,4-Difluorophenoxy)-5,5-dimethyl-4-(4-(methylsulfonyl)phenyl)-5H-furan-2-one Step 1:

2-Methyl-1-1-(4-(methylthio)phenyl)-propan-1-one

To a suspension of aluminum chloride (136 g, 1.02 mol) in chloroform (1.0L) cooled to −10° C., was added dropwise isobutyrylchloride (115 mL, 1.10 mol). Then thioanisole (100 mL, 0.85 mol) was added dropwise. Upon completion of addition the reaction was allowed to proceed at r.t. for 1.5 h. The reaction was cooled to 10° C. and quenched by addition of water (750 mL). The organic layer was separated, washed with water (2×500 mL), saturated $NaHCO_3$ solution(2×500 mL), brine (1×500 mL), and then dried over $Na_2SO_4$. After concentration in vacuo., the resulting crude product crystallized upon standing under high vacuum for 30 min to give the title compound as a brown solid.

Step 2:

2-Hydroxy-2-methyl-1-(4-(methylthio)phenyl)propan-1-one

To a solution of 2-methyl-1-(4-(methylthio)phenyl)propan-1-one (28.5 g, 147 mmol, Step 1), Aliquat 336 (11.0 mL, 24 mmol) and carbon tetrachloride (21 mL, 218 mmol) in toluene (43 mL) was added sodium hydroxide (12.9 g, pellets, 322 mmol). The reaction was stirred at 15° C. for 2 h and then at r.t. for 16 h. The reaction was diluted with water (100 mL), brine (100 mL) and EtOAc (300 mL). The aqueous phase was acidified with 1N HCl and extracted with EtOAc (100 mL). The combined organic layers were dried over $Na_2SO_4$ and concentrated. The crude product was purified by silica gel chromatography eluted with 15% EtOAc in hexane to give the title compound as a thick syrup.

Step 3:

2-Hydroxy-2-methyl-1-(4-(methylsulfonyl)phenyl)propan-1-one

To a cold (4° C.) solution of 2-hydroxy-2-methyl-1-(4-(methylthio)phenyl)propan-1-one (45.0 g, 214 mmol, Step 2) in t-butanol (500 mL) and $CH_2Cl_2$ (500 mL) was added a solution of OXONE™ (194 g, 316 mmol) in water (1.4L). The resulting suspension was stirred at r.t. for 18 h. The reaction was diluted with EtOAc (400 mL) and the layers were separated. The aqueous layer was extracted with EtOAc (2×250 mL). The combined organic layers were dried over $Na_2SO_4$ and concentrated in vacuo. The crude product was dissolved in diethyl ether (250 mL), hexane was added (150 mL) and the product was swished for 2 h. The product was- collected by filtration to give the title compound as a yellow solid.

Step 4

3-(3,4-Difluorophenoxy)-5,5-dimethyl-4-(4-(methylsulfonyl)phenyl)-5H-furan-2-one A solution of 3,4-difluorophenoxyacetic acid (0.51 g, 2.73 mmol), 2-hydroxy-2-methyl-1-(4-(methylsulfonyl)phenyl) propan-1-one (0.5 g, 2.1 mmol, Step 3), CMC (1.13 g, 2.73 mmol) and DMAP (15 mg, 0.10 mmol) in dichloromethane (12 ml) was stirred at r.t. for 18 hrs. Then, DBU (0.63 ml, 4.2 mmol) was added and the reaction mixture was refluxed for 3 h. After cooling to r.t. the mixture was extracted with ethyl acetate and washed successively with water, 1N HCl and brine. The organic layer was dried over $MgSO_4$, filtered and the solvent evaporated under vacuum. The residue was triturated in a mixture of ethyl acetate and hexane affording the title compound as a solid. M.P.: 93–95° C.

$^1H$ NMR ($CD_3COCD_3$) ∂ 1.77 (6H, s), 3.15 (3H, s), 6.93–6.97 (1H, m), 7.12–7.29 (2H, m), 7.92 (2H, d), 8.04 (2H, d).

Analysis calculated for $C_{19}H_{16}F_2O_5S$: C, 57.86; H, 4.09; Found: C, 57.77; H, 4.28

EXAMPLE 2
3-(3-Fluorophenoxy)-5,5-dimethyl-4-(4-(methylsulfonyl)phenyl)-5H-furan-2-one Following the procedure described for example 1, the title compound was prepared from 3-fluorophenoxyacetic acid. M.P.: 136–138° C.

$^1$H NMR (CD$_3$COCD$_3$) ∂ 1.79 (6H, s), 3.15 (3H, s), 6.85–6.94 (3H, M), 7.31–7.86 (1H, m), 7.93 (2H, d), 8.03 (2H,d).

EXAMPLE 3
3-(3,5-Difluorophenoxy)-5,5-dimethyl-4-(4-(methylsulfonyl)phenyl)-5H-furan-2-one Following the procedure described for example 1, the title compound was prepared from 3,5-difluorophenoxyacetic acid. M.P.: 159–161° C.

$^1$H NMR (CD$_3$COCD$_3$) ∂ 1.80 (6H, s), 3.17 (3H, s), 6.78–6.84 (3H, m), 7.96 (2H, d), 8.06 (2H, d).

Analysis calculated for $C_{19}H_{16}F_2O_5S$: C, 57.86; H, 4.09; Found: C, 57.66; H, 4.30

EXAMPLE 4
3-Phenoxy-5,5-dimethyl-4-(4-(methylsulfonyl)phenyl)-5H-furan-2-one

Step 1
3-Phenoxy-5,5-dimethyl-4-(4-(methylthio)phenyl)-5H-furan-2-one

Following the procedure described for example 1, Step 4, the title compound was prepared from phenoxyacetic acid and 2-hydroxy-2-methyl-1-(4-(methylthio)phenyl)propan-1-one (example 1, Step 4).

$^1$H NMR (CD$_3$COCD$_3$) ∂ 1.79 (6H, s), 2.51 (3H, s), 7.03–7.10 (3H, m), 7.30–7.37 (4H, m), 7.72 (2H, d).

Step 2
3-Phenoxy-5,5-dimethyl-4-(4-(methylsulfonyl)phenyl)-5H-furan-2-one

The compound obtained in Step 1 (150 mg, 0.46 mmol) was stirred in dichloromethane (5 mL) with 3-chloroperoxybenzoic acid (250 mg, 1.38 mmol) for 18 hrs. The reaction mixture was diluted with ethyl acetate, washed with saturated sodium bicarbonate, brine, dried over MgSO$_4$, filtered and the solvent evaporated under vacuum. The residue was triturated in Et$_2$O to afford the title compound. M.P.: 135–136° C.

$^1$H NMR (CD$_3$COCD$_3$) ∂ 1.78 (6H, s), 3.14 (3H, s), 7.05–7.08 (3H, m), 7.28–7.30 (2H, m), 7.92 (2H, d), 8.01 (2H, d).

Analysis calculated for $C_{19}H_{18}O_5S$: C, 63.67; H, 5.06; S, 8.95; Found: C, 64.02; H, 5.10: S, 8.84

EXAMPLE 5
3-(2,4-Difluorophenoxy)-5,5-dimethyl-4-(4-(methylsulfonyl)phenyl)-5H-furan-2-one Step 1
2-Bromoacetic acid, 2-methyl-1-(4-(methylsulfonyl)phenyl)propan-1-one ester To a 0° C. solution of 2-hydroxy-2-methyl-1-(4-(methylsulfonyl)phenyl)propan-1-one (4.0 g, 16.5 mmol, example 1, Step 3) in dichloromethane (100 mL) was added pyridine (23.5 mL, 291 mmol) and bromoacetyl bromide (24.9 mL, 285.3 mmol) portionwise over 2 hrs. The reaction mixture was allowed to warm to r.t. and stirred for a further hour. The mixture was diluted with dichloromethane, washed with 1N HCl, brine, filtered through cotton and the solvent was evaporated under vacuum. Purification by silica gel chromatography (40% EtOAc/Hex.) provided 3.50 g of the title compound.

$^1$H NMR (CD$_3$COCD$_3$) ∂ 1.75 (6H, s), 3.20 (3H, s), 4.00 (2H, s), 8.05 (2H, m), 8.25 (2H, m).

Step 2
2-(2,4-Difluorophenoxy)acetic acid 2-methyl-1-(4-(methylsulfonyl)phenyl)propan-1-one-2-yl ester Sodium hydride, 60% dispersion (66 mg, 1.66 mmol), was rinsed with hexane, suspended in 7 mL of DMF and cooled to 0° C. To this suspension was added 2,4-difluorophenol (170 μL, 1.79 mmol). After 5 minutes at 0° C., 2-bromoacetic acid 2-methyl-1-(4-(methylsulfonyl)phenyl)propan-1-one ester (Step 1) (233 mg, 1.79 mmol) was added and the reaction mixture was stirred for 30 minutes. Dichloromethane was added and the mixture was washed with 1N HCl and the organic solvent was evaporated under vacuum. The residue was dissolved in 25%EtOAc/Et20 and washed with 1N NaOH, water (2x) brine and dried over MgSO$_4$. After filtration and evaporation of the solvent under vacuum 470 mg of the title compound was obtained.

$^1$H NMR (CD$_3$COCD$_3$) ∂ 1.75 (6H, s), 3.20(3H, s), 4.80 (2H, s), 6.60 (1H, m), 6.75 (1H, m), 7.00 (1H, m), 8.05 (2H, m), 8.20 (2H, m).

Step 3
3-(2,4-Difluorophenoxy)-5,5-dimethyl-4-(4-(methylsulfonyl) phenyl)-5H-furan-2-one To a solution of 2-(2,4-difluorophenoxy)acetic acid 2-methyl-1-(4-(methylsulfonyl)phenyl)propan-1-one-2-yl ester (Step 2) (470 mg, 1.14 mmol) in acetonitrile (7 mL) was added DBU (187 μL, 1.25 mmol) and the resulting solution was heated at 50° C. for 20 minutes. After cooling to r.t. dichloromethane was added and the mixture was washed with 1N HCl, brine, filtered over cotton and the solvent evaporated under vacuum. Purification by silica gel chromatography followed by a swish in EtOAc/Et$_2$O afforded 122 mg of the title compound.

$^1$H NMR (CD$_3$COCD$_3$) ∂ 1.70 (6H, s), 3.15 (3H, s), 6.90 (1H, m), 7.10 (1H, m), 7.30 (1H, m), 7.85 (2H, m), 8.00 (2H, m).

EXAMPLE 6
3-(4-Chlorophenoxy)-5,5-dimethyl-4-(4-(methylsulfonyl)phenyl)-5H-furan-2-one Following the procedure described for example 1, the title compound was prepared from 4-chlorophenoxyacetic acid. M.P.: 113–114° C.

$^1$H NMR (CD$_3$COCD$_3$) ∂ 1.77 (6H, s), 3.15 (3H, s), 7.11 (2H, d), 7.31 (2H, d), 7.91 (2H, d), 8.04 (2H, d)

EXAMPLE 7
3-(3 4-Dichlorophenoxy)-5,5-dimethyl-4-(4-(methylsulfonyl)phenyl-5H-furan-2-one Following the procedure described for example 1, the title compound was prepared from 3,4-dichlorophenoxyacetic acid. M.P.: 144–145° C.

$^1$H NMR (CD$_3$COCD$_3$) ∂ 1.78 (6H, s), 3.15 (3H, s), 7.12–7.15 (1H, m), 7.35–7.36 (1H, s), 7.49 (1H, d), 7.92 (2H, d), 8.04 (2H, d).

EXAMPLE 8
3-(4-Fluorophenoxy)-5,5-dimethyl-4-(4-(methylsulfonyl)phenyl)-5H-furan-2-one Following the procedure described for example 1, the title compound was prepared from 4-fluorophenoxyacetic acid.

$^1$H NMR (CD$_3$COCD$_3$) ∂ 1.76 (6H, s), 3.14 (3H, s), 7.02–7.13 (4H, m), 7.91 (2H, d), 8.01 (2H, d).

EXAMPLE 9
3-(4-Fluorophenylthio)-5,5-dimethyl-4-(4-(methylsulfonyl)phenyl)-5H-furan-2-one Following the procedure described for example 1, the title compound was prepared from 4-fluorophenylthioacetic acid.

$^1$H NMR (CDCl$_3$) ∂ 1.55 (6H, s), 3.08 (3H, s), 6.85 (2H, m), 7.26 (2H, m), 7.35 (2H, d), 7.94 (2H, d)

EXAMPLE 10

3-(3,5-Difluorophenylthio)-5,5-dimethyl-4-(4-(methylsulfonyl)phenyl)-5H-furan-2-one To a mixture of 3,5-difluorothiophenol (1.0 g) and methyl bromoacetate (1.2 g) in methanol (20 mL) was added 2 mL of a solution of NaOH (0.69 mL of 10N in 3 mL of water), the mixture was stirred for 1 h, then 2 mL of 10N NaOH was added and the mixture stirred for another hour. The solvent was evaporated under vacuum, the residue taken in water and washed with Et$_2$O, then acidified with 1N HCl and extracted with ether. The ether extract was washed with water, dried over MgSO$_4$, filtered and the solvent evaporated under vacuum giving 850 mg of 3,5-difluorophenylthioacetic acid. This acid was reacted as in Step 1 to afford the title compound.

$^1$H NMR (CDCl$_3$) ∂ 1.60 (6H, s), 3.10 (3H, s), 6.60–6.80 (3H, m), 7.45 (2H, d), 8.00 (2H, d).

EXAMPLE 11

3-Phenylthio-5,5-dimethyl-4-(4-(methylsulfonyl)phenyl)-5H-furan-2-one

Following the procedure described for example 1, the title compound was prepared from phenylthioacetic acid. M.P.: 98–114° C.

$^1$H NMR (CD$_3$COCD$_3$) ∂ 1.61 (6H, s), 3.16 (3H, s), 7.21–7.30 (5H, m), 7.61 (2H, d), 7.96 (2H, d).

Analysis calculated for C$_{19}$H$_{18}$O$_4$S$_2$: C, 60.94; H, 4.84; S, 17.12;

Found: C, 61.01; H, 4.90: S, 16.94

EXAMPLE 12

3-(N-Phenylamino)-5,5-dimethyl-4-(4-(methylsulfonyl)phenyl)-5H-furan-2-one

Step 1

2-Phenylaminoacetic acid 2-methyl-1-(4-(methylsulfonyl phenyl)propan-1-one ester Following the procedure described in example 13 Step 1 but using aniline the title compound was obtained.

$^1$H NMR (CD$_3$COCD$_3$) ∂ 1.70 (6H, s), 3.15 (3H, s), 3.95 (2H, br s), 5.15 (1H, br s), 6.40 (2H, m), 6.55 (1H, m), 7.00 (2H, m), 8.00 (2H, m), 8.25 (2H, m).

Step 2

3-N-Phenylamino-5,5-dimethyl-4-(4-(methylsulfonyl)phenyl)-5H-furan-2-one Following the procedure described in example 13 Step 2 but using 2-phenylaminoacetic acid 2-methyl-1-(4-(methylsulfonyl)phenyl) propan-1-one ester the title compound was obtained.

$^1$H NMR (CD$_3$COCD$_3$) ∂ 1.65 (6H, s), 3.05 (3H, s), 6.70 (3H, m), 6.95 (2H, m), 7.25 (1H, br s), 7.50 (2H, m), 7.75 (2H, m).

EXAMPLE 13

3-(N-Methyl-N-phenylamino)-5 5-dimethyl-4-(4-(methylsulfonyl)phenyl)-5H-furan-2-one Step 1

2-(N-Phenyl-N-methylamino)acetic acid 2-methyl-1-(4-(methylsulfonyl)phenyl)propan-1-one ester To a solution of 2-bromoacetic acid 2-methyl-1-(4-(methylsulfonyl)phenyl)propan-1-one ester (example 5, Step 1) (1.0 g, 2.75 mmol) in toluene (2.5 mL) was added N-methylaniline (3.0 mL, 27.5 mmol) and the resulting solution was heated at 115° C. for 16 hrs. After cooling to r.t. the reaction mixture was washed with brine and filtered through cotton. Purification by silica gel chromatography provided 850 mg of the title compound.

Step 2

3-(N,-Methyl-N-phenylamino)-5,5-dimethyl-4-(4-(methylsulfonyl) phenyl)-5H-furan-2-one To a solution of 2-(N-phenyl-N-methylamino)acetic acid 2-methyl-1-(4-(methylsulfonyl)phenyl)propan-1-one ester (700 mg, 1.80 mmol) in acetonitrile (3 mL) was added DBU (2.7 mL, 18.0 mmol) and the resulting solution was heated at 60° C. for 1 h. After cooling to r.t. dichloromethane was added and the mixture was washed with 1N HCl, brine and filtered through cotton and the solvent was evaporated under vacuum. Purification by silica gel chromatography followed by swish in EtOAc/Hex. afforded 266 mg of the title compound.

$^1$H NMR (CD$_3$COCD$_3$) ∂ 1.70 (6H, s), 3.05 (3H,s), 3.15 (3H, s), 6.70 (1H, m), 6.80 (2H, m), 7.10 (2H, m), 7.65 (2H, m), 7.90 (2H, m)

EXAMPLE 14

3-Cyclohexyloxy-5 5-dimethyl-4-(4-(methylsulfonyl) phenyl -5H-furan-2-one

Step 1

2-Bromo-2-methyl-1-(4-(methylsulfonyl)phenyl)propan-1-one

To a solution of 2-methyl-1-(4-(methylthio)phenyl) propan-1-one (example, 1, Step 1) (417.94 g) in ethyl acetate (1.2L) and cyclohexane (1.7L) was added bromine (110 mL) portionwise. After stirring for 10 min the mixture was washed with water, saturated sodium bicarbonate and brine. To this mixture was then added sodium tungstate (6.7 g), Aliquat 336 (25 g) and water (200 mL). The mixture was then heated to 50° C. and hydrogen peroxide (30%, 600 mL) was added slowly. Ethyl acetate and water were then added to the mixture and the organic layer separated, washed with water, dried over sodium sulfate, filtered and the title compound crystalized and was collected by filtration.

Step 2

2-Cyclohexyloxyacetic acid 2-methyl-1-(4-(methylsulfonyl) phenyl)propan-1-one ester A solution of 2-cyclohexyloxyacetic acid (1.74 g, 11 mmol), 2-bromo-2-methyl-1-(4-(methylsulfonyl)phenyl) propan-1-one (3.05 g, 10 mmol) and diisopropylethylamine (2.20 g, 17 mmol) in 30 mL of ethanol was refluxed for 15 h. The solvent was evaporated and the residue dissolved in water and extracted with EtOAc, washed with 5% HCl, saturated sodium bicarbonate, brine and dried over MgSO$_4$, filtered and the solvent evaporated under vacuum. Purification by silica gel chromatography afforded 3.0 g of the title compound.

Step 3

3-Cyclohexyloxy-5 5-dimethyl-4-(4-(methylsulfonyl) phenyl)-5H-furan-2-one

A solution of the ester from the previous step (492 mg, 1.29 mmol) and DBU (1 mL) in 5 mL of acetonitrile was heated at reflux for 15 h.. To the cooled solution was added 5% HCl and the mixture was extracted with EtOAc, washed with a saturated solution af ammonium chloride and dried over MgSO$_4$, filtered and the solvent evaporated under vacuum. Purification by silica gel chromatography afforded the title compound.M.P.: 143–144° C.

$^1$H NMR (CD$_3$COCD$_3$) ∂ 1.20–1.35 (3H, m), 1.40–1.50 (3H, m), 1.66 (6H, s), 1.60–1.70 (2H, m), 1.85–1.95 (2H, m), 3.20 (3H, s), 4.85 (1H, m), 8.00–8.10 (4H, m)

Analysis calculated for C$_{19}$H$_{24}$O$_5$S: C, 62.62; H, 6.64;

5 Found: C, 62.28; H, 6.57

EXAMPLE 15
3-Phenylthio-4-(4-(methylsulfonyl)phenyl)-5H-furan-2-one

At 0° C., triethylamine (335 μL) was added to a solution of thiophenoxyacetic acid (161 mg) and 2-bromo-1-(4-(methylsulfonyl)phenyl) ethanone (272 mg, WO 9500501, example 9, Step 1) in 5 mL of acetonitrile and the mixture was stirred at 0° C. for 1 h. The reaction mixture was then cooled to −20° C. and DBU (265 μL) was added. The mixture was stirred for 30 min. at −20° C. and was quenched by addition of 1N HCl. The product was extracted with EtOAc, dried over sodium sulfate and partially purified by silica gel chromatography. The impure product was recrystalized from EtOAc/Hexane to afford the title compound as a solid $^1$H NMR (CDCl$_3$) ∂ 3.10 (3H, s), 5.25 (2H, s), 7.24–7.38 (5H, m), 7.93 (2H, d), 8.03 (2H, d).

Analysis calculated for C$_{17}$H$_{14}$O$_4$S$_2$: C, 58.94; H, 4.07; Found: C, 58.88; H, 4.18

EXAMPLE 16
3-Benzyl-5,5-dimethyl-4-(4-(methylsulfonyl)phenyl)-5H-furan-2-one Step 1

3-Phenylpropanoic acid 2-methyl-1-(4-(methylthio)phenyl) propan-1-on-2-yl ester

To a −30° C. solution of 2-hydroxy-2-methyl-1-(4-(methylthio)phenyl)propan-1-one (1.05 g, example 1, Step 2) in dichloromethane (20 mL) was added 3-phenylpropionyl chloride (1.68 g) in dichloromethane (10 mL) followed by pyridine (791 mg) and the mixture was allowed to warm up slowly to 25° C. and stirred for 12 h. Ethyl acetate was added to the mixture and it was washed with 1N HCl, brine, dried over magnesium sulfate filtered and the solvent was evaporated under vacuum. Purification by silica gel chromatography afforded 1.36 g of the title compound.

$^1$H NMR (CD$_3$COCD$_3$) ∂ 1.65 (6H, s), 2.50 (3H, s), 2.55–2.65 (2H, t), 2.75–2.85( 2H, t), 7.10–7.40 (7H, m), 7.90–8.00 (2H, d)

Step 2

3-Benzyl-5,5-dimethyl-4-(4-(methylthio)phenyl)-5H-furan-2-one

To a 0° C. solution of the ester from the previous step (1.14 g) in DMF (10 mL) and THF (2 mL) was added sodium hydride (120 mg of 80% dispersion) and the mixture was stirred for 2 h at 25° C. Then it was poured over icy 1N HCl and extracted with ethyl acetate, the organic layer was washed with water, brine, dried over MgSO$_4$ and the solvent evaporated under vacuum. The residue was purified by silica gel chromatography affording 596 mg of the title compound.

$^1$H NMR (CD$_3$COCD$_3$) ∂ 1.50 (6H, s), 2.55 (3H, s), 3.50 (2H, s), 7.05–7.30 (7H, m), 7.35–7.40 (2H, d)

Step 3

3-Benzyl-5,5-dimethyl-4-(4-(methylsulfonyl)phenyl-5H-furan-2-one

To a 0° C. solution of the lactone from the previous step (596 mg) in dichloromethane (10 mL) and methanol (5 mL) was added portionwise MMPP (2×590 mg) and the mixture was allowed to slowly warm-up to 25° C. After 2 h. at 25° C. the mixture was partitioned between dichloromethane and water, the organic layer was washed with brine, dried over MgSO$_4$, filtered and the solvent evaporated under vacuum. The residue was swished in ether to yield 530 mg of the title compound. Analysis calculated for C$_{20}$H$_{20}$O$_4$S: C, 67.40; H, 5.65;

Found: C, 67.28; H, 5.78

EXAMPLE 17
3-(3,4-Difluorophenylhydroxymethyl)-5,5-dimethyl-4-(4-(methylsulfonyl) phenyl)-5H-furan-2-one Using a procedure similar to the Steps 1, 2 and 3 of example 19 but using 3,4-difluorobenzaldehyde as an electrophile the title compound was obtained.

$^1$H NMR (CD$_3$COCD$_3$) ∂ 1.45 (6H, s), 3.15 (3H, s), 5.00 (1H, bs), 5.50 (1H, bs), 6.45–6.55 (2H, d), 7.00–7.30 (3H, m), 7.95–8.05 (2H, d).

EXAMPLE 18
3-(3,4-Difluorobenzoyl)-5,5-dimethyl-4-(4-(methylsulfonyl)phenyl)-5H-furan-2-one Using a procedure similar to Step 4 of example 19 and using the compound obtained in example 17, the title compound was obtained $^1$H NMR (CD$_3$COCD$_3$) ∂ 1.75 (6H, s), 3.10 (3H, s), 7.35–7.45 (1H, m), 7.65–7.75 (2H, d), 7.75–7.90 (2H, m), 7.95–8.05 (2H, d).

EXAMPLE 19
3-Benzoyl-5,5-dimethyl-4-(4-(methylsulfonyl)phenyl)-5H-furan-2-one Step 1

Acetic acid 2-methyl-1-(4-methylthiophenyl)propan-1-on-2-yl ester

To a 0° C. solution of 2-hydroxy-2-methyl-1-(4-(methylthio)phenyl)propan-1-one (150 g, example 1, Step 2), DBU (217 g) and DMAP (7 g) in dichloromethane (850 mL) was added acetyl chloride (112.2 g) dropwise and the mixture was stirred for 6 h. at 25° C. More DBU (32.5 g) was added and the mixture was stirred an additionnal 16 h. The reaction mixture was poured over 2N HCl (800 mL) and the organic layer was separated, washed with a saturated solution of NaHCO$_3$, dried over MgSO$_4$, filtered and the solvent was evaporated under vacuum. The residue was swished in Et$_2$O, then 25% ethyl acetate in hexane, then filtered and dried giving 74 g of the title compound.

$^1$H NMR (CD$_3$COCD$_3$) ∂ 1.60 (6H, s), 1.90 (3H, s), 2.55 (3H, s), 7.30 (2H, d), 8.00 (2H, d).

Step 2

5,5-Dimethyl-4-(4-(methylthio)phenyl)-5H-furan-2-one

To a 0–5° C. solution of the ester from the previous step (74 g) in DMF (1.2L) was added NaH (9 g, 80% dispersion) portionwise and the mixture was stirred for 3 h. Saturated aqueous NH$_4$Cl was added slowly. The mixture was then partitioned between ethyl acetate and water, the organic layer was washed with water, dried with Na$_2$SO$_4$, filtered and the solvent was evaporated under vacuum. The residue was swished in 30% ethyl acetate/ hexane to yield the title compound (38 g).

$^1$H NMR (CD$_3$COCD$_3$) ∂ 1.70 (6H, s), 2.55 (3H, s), 6.40 (1H, s), 7.40 (2H, d), 7.70 (2H, d).

Step 3

5,5-Dimethyl-4-(4-(methylsulfonyl)phenyl)-3-(phenylhydroxymethyl) -5H-furan-2-one To a −78° C. solution of the lactone (702 mg) obtained in the previous step in THF was added 0.67M LDA (9.25 mL) and the mixture was reacted for 5 min. Benzoyl chloride (913 mg) was then added at −78° C. and after 15 min the mixture was poured over icy 1N HCl. The organic material was extracted with ethyl acetate, washed with brine, dried with MgSO$_4$, filtered and the solvent was evaporated under vacuum. The residue was dissolved in dichloromethane (10 mL) and methanol (10 mL) and the solution cooled to 0° C. MMPP (4.9 g) was added and the mixture warmed and stirred at 25° C. for 2 h. The mixture was poured over icy water and the organic layer was dried over MgSO$_4$, filtered and the solvent evaporated under vacuum. The residue was purified by silica gel chromatography to yield 190 mg of compound which was dissolved in methanol(2 mL) and THF (1 mL), cooled to 0° C. and a catalytic amount of NaOH was added. The mixture was poured in icy water and extracted with ethyl acetate, the organic layer was washed with brine, dried over $MgSO_4$, filtered and the solvent evaporated under vacuum.

Step 4
3-Benzoyl-5,5-dimethyl-4-(4-(methylsulfonyl)phenyl)-5H-furan-2-one

The residue was dissolved in acetone (3 mL), and Jone's reagent (3M, 150 µL) was added. The mixture was stirred for 1 h. then poured over icy water and extracted with ethyl acetate, the organic layer was washed with brine, dried over $MgSO_4$, filtered and the solvent was evaporated under vacuum. The residue was swished in ether to yield the title compound (123 mg).

Analysis calculated for $C_{20}H_{18}O_5S$: C, 64.85; H, 4.84; Found: C, 64.63; H, 5.23

EXAMPLE 20
4-(4-(Methylsulfonyl)phenyl)-3-phenoxy-1-oxaspiror[4,4]non-3-en-2-one Using a procedure similar to the one used in example 1 but using (1-hydroxycyclopentyl)-(4-(methylsulfonyl)phenyl)methanone from example 21, Step 3 and phenoxy-acetic acid the title compound was obtained.

$^1$H NMR ($CDCl_3$) ∂ 1.80–2.30 (8H, m), 3.04 (3H, s), 6.95–7.35 (5H, m), 7.75 (2H, d), 7.95 (2H, d).

EXAMPLE 21
4-(4-(Methylsulfonyl)phenyl-3-phenylthio-1-oxaspiror[4.4]non-3-en-2-one Step 1:
Cyclopentyl-(4-(methylthio)phenyl)methanone To a suspension of anhydrous aluminum chloride (9.3 g, 69.6 mmol) in 58 mL $CHCl_3$ at 0° C. was added dropwise cyclopentanecarbonyl chloride (10.0 g, 75.4 mmol), followed by thioanisole (7.21 g, 58.0 mmol). The ice bath was removed and the mixture was stirred at room temperature for 2 h. Water (200 ml) was added with cooling, the layers were separated and the aqueous layer was extracted with $CHCl_3$ (3×50 mL). The combined aqueous layers were dried over $MgSO_4$, filtered and concentrated. The residue was chromatographed on silica gel (4% EtOAc/hexane) to give 11.9 g of the title ketone (93%).

$^1$H NMR ($CD_3COCD_3$) ∂ 7.94 (d, 2H), 7.36 (d, 2H), 3.79 (q, 1H), 2.56 (s, 3H), 2.00-1.71 (m, 4H), 1.70-1.50 (m, 4H).

Step 2:
(1-Hydroxycyclopentyl)-(4-(methylthio)phenyl)methanone

To a solution of the ketone from Step 1 (7.2 g, 32.7 mmol) in 4.7 ml $CCl_4$ and 9.6 ml toluene was added Aliquat 336 (2.11 g, 5.20 mmol) and powdered NaOH (2.88 g, 71.9 mmol) and the mixture was stirred for 16 h at r.t. To the brown mixture was added 100 ml of 5% aq. HCl and extracted with EtOAc (4×100 ml). The combined organic layers were washed with brine, dried over $MgSO_4$, filtered and concentrated. Chromatography on silica gel (20% EtOAc/hexane) gave 5.4 g of the title compound as a white waxy solid (70%).

$^1$H NMR ($CD_3COCD_3$) ∂ 8.11 (d, 2H), 7.31 (d, 2H), 4.63 (s, 1H, disappears by $D_2O$ wash), 2.56 (s, 3H), 2.24 (m, 2H), 1.89 (m, 4H), 1.71 (m, 2H).

Step 3
(1-Hydroxycyclopentyl)-(4-(methylsulfonyl)phenyl)-methanone

The sulfide obtained in Step 2 (56 g) was dissolved in dichloromethane (800 mL) and methanol (200 mL) and treated with MMPP (139 g) and stirred for 3 h. The organic layer was diluted with dichloromethane, washed with water and brine, dried over $MgSO_4$, filtered and the solvent evaporated to afford the title compound.

Step 4
4-(4-(Methylsulfonyl)phenyl)-3-phenylthio-1-oxaspiro[4,4]non-3-en-2-one

The hydroxyketone from the previous step was reacted with phenylthioacetic acid as in the procedure for example 1, Step 4 to afford the title compound.

$^1$H NMR ($CDCl_3$) ∂ 1.70–2.05 (8H, m), 3.06 (3H, s), 7.10–7.25 (5H, m), 7.35(2H,d),7.90(2H,d).

EXAMPLE 22
4-(2-Oxo-3-phenylthio-1-oxa-spiro[4,4]non-3-en-4-yl) benzenesulfonamide To a solution of 1-(hydroxycyclopentyl)-(4-methylthiophenyl) methanone (52 g, example 21, Step 2) in $CH_2Cl_2$ (400 mL) and methanol (200 mL) at 0° C. was added portionwise MMPP (61 g). After stirring for 3 h the reaction mixture was washed with water, dried over $Na_2SO_4$, filtered and evaporated to dryness to provide the sulfoxide intermediate which (7.56 g) was dissolved in TFAA (100.0 mL) and refluxed for 3 h. The mixture was cooled to 0° C. and 10N NaOH (24 mL), was added dropwise and under nitrogen. After vigorous stirring for 0.5 h, acetic acid (100 mL) and water (20 mL)was added. The mixture was cooled to 0° C. and chlorine gas was bubbled for 20 min. The excess chlorine was removed under vacuum and the mixture was poured over icy water and extracted with ethyl acetate. The extracts were washed with water, saturated $NaHCO_3$ and brine. The organic layer was cooled to 0° C. and t-butylamine (10 mL) was added and stirred for 1 h. The reaction mixture was diluted with water and neutralized with 6N HCl, washed with brine, dried over $MgSO_4$ filtered and the solvent evaporated under vacuum. The residue was swished in ether. This hydroxyketone (325 mg) was then reacted as in example 1, Step 4 using phenylthioacetic acid (200 mg)to w give an intermediate (300 mg) which was stirred in dichloromethane (2 mL) and trifluoroacetic acid (8mL) for 18h. The solvents were then evaporated under vacuum and the residue was recrystallized from ethanol to afford the title compound.

$^1$H NMR ($CD_3COCD_3$) ∂ 1.65–2.20 (8H, m), 6.68 (2H, br s), 7.25 (5H, m), 7.55 (2H, d), 7.95 (2H, d).

EXAMPLE 23
3-(4-Fluorobenzyl)-5,5-dimethyl-4-(4-(methylsulfonyl) phenyl)-5H-furan-2-one Using a procedure similar to the one for example 16 but using 3-(4-fluorophenyl)propionyl chloride the title compound was obtained.

$^1$H NMR ($CD_3COCD_3$) ∂ 1.50 (6H, s), 3.15 (3H, s), 4.45 (2H, s), 7.05–7.15 (2H, m), 7.50–7.60 (2H, d), 7.85–7.95 (2H, m), 7.95–8.05 (2H, d).

EXAMPLE 24
3-(3,4-Difluorophenoxy)-5-methoxy-5-methyl-4-(4-(methylsulfonyl)phenyl)-5H-furan-2-one Step 1
2-Bromo-1-(4-(methylsulfonyl)phenyl)propan-1-one Following a procedure similar to the one used in example 1, Step 1 but using propionyl chloride, 1-(4-(methylsulfonyl)phenyl)propan-1-one was obtained. A solution of this compound (163.4 g) in chloroform (2.2L) was then cooled to 0° C. and treated with bromine (40 mL in 200 mL $CHCl_3$) and concentrated HBr (10 mL). The reaction mixture was washed with water, saturated sodium bicarbonate and brine, dried over sodium sulfate, filtered and the solvent evaporated under vacuum. The residue was swished in ethyl acetate: hexane 1:1 to give the title compound (191 g).

Step 2

5-Hydroxy-5-methyl-4-(4-(methylsulfonyl)phenyl)-3-phenlthio-5H-furan-2-one

To a mixture of 2-bromo-1-(4-(methylsulfonyl)phenyl) propan-1-one (6.0 g, 20.6 mmol) and thiophenoxyacetic acid (3.8 g, 22.6 mmol) in acetonitrile (60 mL) was added triethylamine (4.0 mL, 28.8 mmol). The mixture was stirred at r.t. for 3 h. T.L.C. showed no bromoketone remaining and DBU (4.0 mL) was added. The mixture was stirred at r.t. for 1 h., then air was bubbled through the mixture for another hour. After dilution with water, the mixture was extracted with EtOAc. The EtOAc extract was washed with 1N aquous HCl, brine, dried over $MgSO_4$, filtered and the solvent evaporated under vacuum. The residue was swished in $Et_2O$ to give the title compound (6.0 g) as a pale yellow powder.

$^1$H NMR ($CD_3COCD_3$) $\partial$ 1.68 (3H, s), 3.16 (3H, s), 6.86 (1H, s), 7.35 5H, m), 7.78 (2H, d), 7.98 (2H, d).

Step 3

5-Methoxy-5-methyl-4-(4-(methylsulfonyl)phenyl)-3-phenylthio-5H-furan-2-one

The alcohol (2.5 g, 6.6 mmol) from the previous step was dissolved in methanol (100 mL), THF (20 mL) and concentrated HCl (5 mL) and heated at 70° C. for 24 h. After cooling to 0° C. the precipitate formed was filtered, washed with methanol and dried under vacuum to give the title compound (2.0 g) as a yellow solid.

$^1$H NMR ($CD_3COCD_3$) $\partial$ 1.65 (3H, s), 3.15 (3H, s), 3.40 (3H, s), 7.18–7.40 (5H, m), 7.88 (2H, d), 7.98 (2H, d).

Step 4

3-(3,4-Difluorophenoxy)-5-methoxy-5-methyl-4-(4-(methylsulfonyl)phenyl)-5H-furan-2-one To a solution of the compound obtained in the previous step (2.0 g, 5.1 mmol) in dichloromethane (100 mL) at r.t. was added mCPBA (4.0 g, Aldrich 57–86%, ~16 mmol). The mixture was stirred at r.t. for 3 h and more mCPBA (2.0 g) was added. After stirring for another hour the mixture was washed with 1N NaOH, brine, dried and concentrated under vacuum to yield a disulfone as a white foam (2.0 g). To a solution of 3,4-difluorophenol (2.0 g, 14.9 mmol) in DMF was added 1ON NaOH (1 mL, 10 mmol). After 30 min. a solution of the above disulfone (2.0 g, 4.7 mmol) in DMF was added. The mixture was heated at 80–85° C. for 1.5 h. After cooling the mixture was diluted with water, extracted with EtOAc, the organic extracts were washed with 1N NaOH, 1N HCl, brine, dried over $MgSO_4$, filtered and the solvent evaporated under vacuum. Purification by silica gel chromatography afforded the title compound as a white solid (600 mg).

$^1$H NMR ($CD_3COCD_3$) $\partial$ 1.86 (3H, s), 3.16 (3H, s), 3.40 (3H, s), 6.95–7.40 (3H, m), 8.08 (2H, d), 8.16 (2H, d).

EXAMPLE 25

3-(5-Chloro-2-pyridyloxy)-5,5-dimethyl-4-(4-(methylsulfonyl)phenyl)-5H-furan-2-one To a mixture of 2-chloroacetic acid 2-methyl-1-(4-(methylsulfonyl)phenyl)propan-1-one ester (1.0 g, 3.13 mmol, prepared similarly to the compound of example 5, Step 1) and 5-chloro-2-pyridinol (0.41 g, 3.16 mmol) in $CH_3CN$ (20 mL) was added DBU (1.5 mL, 10.0 mmol) at r.t. The mixture was stirred for 1h, then heated at 65–70° C. for 3 h. The volatile solvents were removed in vacuo. The residue was chromatographed over silica gel and eluted with hexane:EtOAc (1:1) to yield a colorless oily residue which was swished in $Et_2O$ to provide the title compound as a white powder (230 mg).

$^1$H NMR ($CD_3COCD_3$) $\partial$ 1.80 (6H, s), 3.20 (3H, s), 7.18 (1H, d), 7.94 (3H, m), 8.06 (2H, d), 8.19 (1H, d).

EXAMPLE 26

3-(2-pyridyloxy)-5,5-dimethyl-4-(4-(methylsulfonyl)phenyl)-5H-furan-2-one

Following the procedure described for example 25, the title compound was prepared from 2-hydroxypyridine.

$^1$H NMR ($CD_3COCD_3$) $\partial$ 1.78 (6H, s), 3.15 (3H, s), 7.00–7.20 (2H, m), 7.80–8.20 (6H, m).

EXAMPLE 27

3-(6-Methyl-2-pyridyloxy)-5,5-dimethyl-4-(4-(methylsulfonyl)phenyl)-5H-furan-2-one Following the procedure described for example 25, the title compound was prepared from 2-hydroxy-6-methylpyridine.

$^1$H NMR ($CD_3COCD_3$) $\partial$ 1.75 (6H, s), 3.14 (3H, s), 6.85 (1H, d), 7.00 (1H, d), 7.70 (1H, t), 7.90 (2H, d), 8.00 (2H, d).

EXAMPLE 28

3-(3-Isoquinolinoxy)-5.5-dimethyl-4-(4-(methylsulfonyl)phenyl)-5H-furan-2-one

Following the procedure described for example 25, the title compound was prepared from 3-hydroxyisoquinoline.

$^1$H NMR ($CD_3COCD_3$) $\partial$ 1.80 (6H, s), 3.14 (3H, s), 7.40–8.10 (9H, m), 9.00 (1H, s).

EXAMPLE 29

3-(4-(Methylsulfonyl)phenyl)-2-phenoxycyclopent-2-enone

Step 1

1-(4-(Methylthio)phenyl)-5-phenoxypenta-1,4-dione

To a mixture containing 1-phenoxybut-3-en-2-one (1.0 g) (A. G. Schultz, R. D. Lucci, W. Y. Fu, M. H. Berger, J. Erhardt and W. K. Hagmann, J. Amer. Chem. Soc. 100, 2150, (1978)), 4-(methylthio)benzaldehyde (0.62 g) and triethylamine (0.343 mL) in 1,4-dioxane (20 mL) was added 3-benzyl-5-(2-hydroxyethyl)-4-methylthiazolium chloride (110 mg). After stirring 4 h. at 100° C. the reaction mixture was extracted with EtOAc, dried over $MgSO_4$, filtered and the solvent evaporated under vacuum. The residue was purified by silica gel chromatography (20% EtOAc/Hexane) to afford 140 mg of the title compound as an oil.

Step 2

3-(4-(Methylthio)phenyl)-2-phenoxycyclopent-2-enone

To the diketone of Step 1 (120 mg) in methanol (80 mL) was added DBU (0.1 mL). The resulting mixture was heated at 60° C. for 18 h. The methanol was then evaporated and to the crude mixture was added saturated aqueous ammonium chloride, the mixture was then extracted with EtOAc, the organic layer was dried over $MgSO_4$, filtered, and the solvent evaporated under vacuum. The residue was purified by silica gel chromatography (20% EtOAc/hexane) to afford the title compound.

Step 3

(4-(Methylsulfonyl)phenyl)-2-phenoxycyclopent-2-enone

To the compound obtained in Step 2 (60 mg) in dichloromethane (4.5 mL) and methanol (2.4 mL) was added Oxone® (450 mg) in water (1 mL) and the reaction mixture was stirred for 1 h. Water was added to the mixture which was then extracted with dichloromethane, the organic layers were combined and dried over $MgSO_4$, filtered and the solvent evaporated under vacuum. Purification by silica gel chromatograohy afforded the title compound.

$^1$H NMR ($CD_3COCD_3$) $\partial$ 2.65 (2H, t), 3.15 (3H, s), 3.20 (2H, t); 7.05–7.35 (5H, m), 8.10 (4H, m).

EXAMPLE 30
3-(4-(Methylsulfonyl)phenyl)-2-(3,4-difluorophenoxy)cyclopent-2-enone $^1$H NMR (CD$_3$COCD$_3$) ∂ 2.05 (2H, t), 3.15 (3H, s), 3.20 (2H, t), 6.90 (1H, m), 7.10 (1H, m), 7.25 (1H, m), 8.10 (4H, m).

What is claimed is:

1. A compound of Formula I

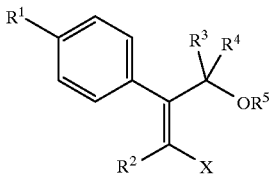

or pharmaceutically acceptable salts thereof wherein:

X is selected from the group consisting of:
(a) CH$_2$OR$^6$,
(b) C(O)R$^7$,
(c) CH$_2$C(O)CH$_3$ and
(d) CH$_2$CH$_2$COR$^7$;

R$^1$ is selected from the group consisting of:
(a) S(O)$_2$CH$_3$,
(b) S(O)$_2$NH$_2$,
(c) S(O)$_2$NHC(O)CF$_3$,
(d) S(O)(NH)CH$_3$,
(e) S(O)(NH)NH$_2$ and
(f) S(O)(NH)NHC(O)CF$_3$;

R$^2$ is selected from the group consisting of:
(a) NR$^8$R$^9$,
(b) SR$^9$,
(c) OR$^9$,
(d) R$^9$ and
(e) a mono-, di-, tri- or tetra-substituted heterocycloalkyl group of 5, 6 or 7 members which contains 1 or 2 heteroatoms chosen from O, S, or N and optionally contains a carbonyl group or a sulfonyl group,the said substituents are selected from the group consisting of
(1) halo,
(2) C$_{1-10}$alkyl,
(3) C$_{1-10}$alkoxy,
(4) C$_{1-10}$alkylthio,
(5) CN,
(6) CF$_3$, and
(7) C(CH$_3$)$_2$OH;

R$^3$ and R$^4$ are each independently C$_{1-10}$alkyl, CH$_2$OR$^8$, CN, or C$_{1-6}$fluoroalkyl, unsubstituted or mono- or di-substituted phenyl, unsubstituted or mono or di-substituted benzyl, unsubstituted or mono- or di-substituted heteroaryl, unsubstituted or mono or di-substituted heteroarylmethyl, wherein the substituents are selected from the group consisting of:
(1) halo,
(2) C$_{1-10}$alkyl,
(3) C$_{1-10}$alkoxy,
(4) C$_{1-10}$alkylthio,
(5) CN and
(6) CF$_3$, or R$^3$ and R$^4$ together with the carbon to which they are attached may form a saturated monocyclic ring of 3, 4, 5, 6, or 7 members which may optionally contain one or two heteroatoms chosen from O, S or N;

R$^5$ is selected from the group consisting of:
(a) hydrogen,
(b) C$_{1-6}$alkyl and
(c) C(O)R$^{10}$;

R$^6$ is selected from the group consisting of:
(a) hydrogen,
(b) C$_{1-6}$alkyl and
(c) C(O)R$^{10}$;

R$^7$ is selected from the group consisting of:
(a) hydrogen,
(b) OH,
(c) NH$_2$,
(d) OR$^{10}$,
(e) NHR$^{10}$ and
(f) NR$^{10}$R$^{11}$;

R$^8$ is independently selected from the group consisting of:
(a) hydrogen and
(b) R$^9$;

R$^9$ is selected from the group consisting of:
(a) unsubstituted or mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2, 3, or 4 additional N atoms, said substituents are selected from the group consisting of
(1) halo,
(2) C$_{1-10}$alkyl,
(3) C$_{1-10}$alkoxy,
(4) C$_{1-10}$alkylthio,
(5) CN and
(6) CF$_3$, (b) an unsubstituted or a mono- or di- substituted benzoheterocycle in which the heterocycle is a 5, 6, or 7-membered ring which may contain 1 or 2 heteroatoms chosen independently from O, S, or N and which may contain a carbonyl group or a sulfonyl group; the said substituents are selected from the group consisting of:
(1) halo,
(2) C$_{1-10}$alkyl,
(3) C$_{1-10}$alkoxy,
(4) C$_{1-10}$alkylthio,
(5) CN and
(6) CF$_3$, and (c) a mono- or di-substituted bicyclic heteroaryl or 8, 9, or 10 members, containing 2 to 5 heteroatoms chosen independently from O, S or N, and in which each ring contains at least one heteroatom, wherein the substituents are selected from the group consisting of
(1) hydrogen,
(2) halo,
(3) C$_{1-10}$alkyl,
(4) C$_{1-10}$alkoxy,
(5) C$_{1-10}$alkylthio,
(6) CN and
(7) CF$_3$;

R$^{10}$ and R$^{11}$ are independently chosen from the group consisting of:
(a) C$_{1-10}$alkyl
(b) C$_{1-10}$alkyl-CO$_2$R$^{12}$
(c) C$_{1-10}$alkyl-NR$^{12}$R$^{13}$
(d) (CH$_2$CH$_2$O)$_n$R$^{12}$, where n=1 to 200, and
(e) (CH$_2$CH$_2$O)$_n$CH$_2$CH$_2$NR$^{12}$R$^{13}$, where n=1 to 200, or R$^{10}$ and R$^{11}$ together with the nitrogen to which they are attached may form a monocyclic ring of 3, 4, 5, 6, or 7 members which may optionally contain an additional one or two heteroatoms chosen from O, S or N—$R^{12}$;

$R^{12}$ and $R^{13}$ are independently chosen from the group consisting of.
(a) hydrogen and
(b) $C_{1-10}$alkyl.

2. A compound according to claim 1 wherein X is selected from the group consisting of:
(a) $CH_2OR^6$ and
(b) $C(O)R^7$.

3. A compound according to claim 1 wherein $R^2$ is $R^9$.

4. A compound according to claim 2 wherein: X is selected from the group consisting of:
(a) $CH_2OR^6$ and
(b) $C(O)R^7$;

$R^1$ is selected from the group consisting of:
(a) $S(O)_2CH_3$,
(b) $S(O)_2NH2$ and
(c) $S(O)_2NHC(O)CF_3$;

$R^2$ is unsubstituted or mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2, 3, or 4 additional N atoms, said substituents are selected from the group consisting of:
(1) halo,
(2) $C_{1-10}$alkyl,
(3) $C_{1-10}$alkoxy,
(4) $C_{1-10}$alkylthio and
(5) $CF_3$;

$R^3$ and $R^4$ are independently $C_{1-3}$alkyl or $C_{1-3}$fluoroalkyl, or $R^3$ and $R^4$ together with the carbon to which they are attached may form a monocyclic ring of 3, 4, 5, or 6 members which may optionally contain a heteroatom chosen from O, or S;

$R^5$ is selected from the group consisting of:
(a) hydrogen,
(b) $C_{1-3}$alkyl and
(c) $C(O)R^{10}$;

$R^6$ is selected from the group consisting of:
(a) hydrogen,
(b) $C_{1-3}$alkyl and
(c) $C(O)R^{10}$;

$R^7$ is selected from the group consisting of:
(b) OH,
(c) $NH_2$,
(d) $OR^{10}$,
(e) $NHR^{10}$ and
(f) $NR^{10}R^{11}$;

$R^{10}$ and $R^{11}$ are independently chosen from the group consisting of:
(a) $C_{1-3}$alkyl,
(b) $C_{1-6}$alkyl—$CO_2R^{12}$,
(c) $C_{1-6}$alkyl—$NR^{12}R^3$,
(d) $(CH_2CH_2O)_nR^{12}$, where n=1 to 200, and
(e) $(CH_2CH_2O)_nCH_2CH_2NR^{12}R^{13}$, where n=1 to 200, or $R^{10}$ and $R^{11}$ together with the nitrogen to which they are attached may form a monocyclic ring of 3, 4, 5, 6, or 7 members which may optionally contain an additional heteroatom chosen from O, S or N—$R^{12}$;

$R^{12}$ and $R^{13}$ are independently chosen from the group consisting of:
(a) hydrogen and
(b) $C_{1-10}$alkyl.

5. A compound according to claim 2 wherein X is selected from the group consisting of:
(a) $CH_2OR^6$ and
(b) $C(O)R^7$, $R^1$ is selected from the group consisting of:
(a) $S(O)_2CH_3$ and
(b) $S(O)_2NH_2$;

$R^2$ is an unsubstituted or mono-, di- or tri-substituted heteroaryl wherein aryl is selected from the group consisting of:
(1) furanyl,
(2) diazinyl,
(3) imidazolyl,
(4) isooxazolyl,
(5) isothiazolyl,
(6) oxadiazolyl,
(7) oxazolyl,
(8) pyrazolyl,
(9) pyridyl,
(10) pyrrolyl,
(11) tetrazinyl
(12) tetrazolyl.
(13) thiadiazolyl,
(14) thiazolyl,
(15) thienyl,
(16) triazinyl and
(17) triazolyl, and the substituent is selected from the group consisting of:
(1) halo,
(2) $C_{1-3}$alkoxy,
(3) $CF_3$ and
(4) $C_{1-3}$alkyl;

$R^3$ and $R^4$ are independently $C_{1-3}$alkyl or $C_{1-3}$fluoroalkyl;

$R^5$ is selected from the group consisting of:
(a) hydrogen and
(b) methyl;

$R^6$ is selected from the group consisting of:
(a) hydrogen,
(b) $C_{1-3}$alkyl and
(c) $C(O)R^{10}$;

$R^7$ is selected from the group consisting of:
(b) OH,
(c) $NH_2$,
(d) $OR^{10}$,
(e) $NHR^{10}$ and
(f) $NR^{10}R^{11}$;

$R^{10}$ and $R^{11}$ are independently chosen from the group consisting of:
(a) $C_{1-3}$alkyl,
(b) $C_{1-6}$alkyl—$CO_2R^{12}$,
(c) $C_{1-6}$alkyl—$NR^{12}R^{13}$,
(d) $(CH_2CH_2O)_nR^{12}$, where n=1, 2, 3, 4 or 5, and
(e) $(CH_2CH_2O)_nCH_2CH_2NR^{12}R^{13}$; and $R^{12}$ and $R^{13}$ are independently chosen from the group consisting of:
(a) hydrogen and
(b) $C_{1-4}$alkyl.

6. A compound according to claim 1 wherein $R^1$ is $S(O)_2CH_3$.

7. A compound according to claim 5 wherein $R^2$ is an unsubstituted or mono-, di- or tri-substituted heteroaryl wherein aryl is selected from the group consisting of:

(1) furanyl,
(2) diazinyl,
(3) oxazolyl,
(4) pyrazolyl,
(5) pyridyl,
(6) pyrrolyl,
(7) tetrazinyl
(8) tetrazolyl,
(9) thiazolyl and
(10) thienyl,
the substituent is selected from the group consisting of:
(1) halo,
(2) $C_{1-3}$alkoxy,
(3) $CF_3$ and
(4) $C_{1-3}$alkyl.

8. A compound according to claim 1 wherein $R^3$ and $R^4$ is independently chosen from the group consisting of:
(a) methyl and
(b) ethyl.

9. A pharmaceutical composition for treating an inflammatory disease susceptable to treatment with an non-steroidal antiinflammatory agent comprising:
a non-toxic therapeutically effective amount of a compound according to claim 1 and a pharmaceutically acceptable carrier.

10. A pharmaceutical composition for treating cyclooxygenase mediated diseases advantageously treated by an active agent that selectively inhibits COX-2 in preference to COX-1 comprising:
a non-toxic therapeutically effective amount of a compound according to claim 1 and a pharmaceutically acceptable carrier.

11. A method of treating an inflammatory disease susceptable to treatment with an non-steroidal anti-inflammatory agent comprising:
administration to a patient in need of such treatment of a non-toxic therapeutically effective amount of a compound according to claim 1 and a pharmaceutically acceptable carrier.

12. A method of treating cyclooxygenase mediated diseases advantageously treated by an active agent that selectively inhibits COX-2 in preference to COX-1 comprising:
administration to a patient in need of such treatment of a non-toxic therapeutically effective amount of a compound according to claim 1.

* * * * *